(12) United States Patent
Wyatt et al.

(10) Patent No.: US 8,293,767 B2
(45) Date of Patent: *Oct. 23, 2012

(54) 4-(2,6-DICHLORO-BENZOYLAMINO)-1H-PYRAZOLE-3-CARBOXYLIC ACID PIPERIDIN-4-YLAMIDE ACID ADDITION SALTS AS KINASE INHIBITORS

(75) Inventors: Paul Graham Wyatt, Perth (GB); David Charles Rees, Cambridge (GB); Mladen Vinkovic, Cambridge (GB); Gary Trewartha, Stevenage (GB)

(73) Assignee: Astex Therapeutics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/188,887

(22) Filed: Jul. 22, 2011

(65) Prior Publication Data

US 2011/0274616 A1 Nov. 10, 2011

Related U.S. Application Data

(63) Continuation of application No. 11/814,458, filed as application No. PCT/GB2006/000207 on Jan. 20, 2006.

(60) Provisional application No. 60/645,973, filed on Jan. 21, 2005.

(51) Int. Cl.
*A61K 31/445* (2006.01)
*C07D 401/00* (2006.01)

(52) U.S. Cl. ................... 514/326; 514/329; 546/211
(58) Field of Classification Search ............... 514/326, 514/329; 546/211
See application file for complete search history.

(56) References Cited

U.S. PATENT DOCUMENTS

| | | | |
|---|---|---|---|
| 2,917,432 | A | 12/1959 | Timmis et al. |
| 3,046,301 | A | 7/1962 | Phillips et al. |
| 4,005,063 | A | 1/1977 | Gendrich et al. |
| 4,100,274 | A | 7/1978 | Dutta et al. |
| 4,282,361 | A | 8/1981 | Hecht et al. |
| 4,377,687 | A | 3/1983 | Eisenbrand |
| 4,950,668 | A | 8/1990 | Okada et al. |
| 4,978,672 | A | 12/1990 | Bowman et al. |
| 5,002,755 | A | 3/1991 | Mitchell et al. |
| 5,164,196 | A | 11/1992 | Plata et al. |
| 5,502,068 | A | 3/1996 | Lown et al. |
| 5,514,664 | A | 5/1996 | Ulrich |
| 5,877,296 | A | 3/1999 | Hamann et al. |
| 6,020,357 | A | 2/2000 | Pinto et al. |
| 6,066,738 | A | 5/2000 | Dinsmore et al. |
| 6,306,393 | B1 | 10/2001 | Goldenberg |
| 6,455,559 | B1 | 9/2002 | Pevarello et al. |
| 6,878,714 | B2 | 4/2005 | Askew et al. |
| 7,385,059 | B2 | 6/2008 | Berdini et al. |
| 7,745,638 | B2 | 6/2010 | Berdini et al. |
| 7,825,140 | B2 | 11/2010 | Berdini et al. |
| 8,013,163 | B2 * | 9/2011 | Wyatt et al. ............ 546/211 |
| 8,080,666 | B2 | 12/2011 | Berdini et al. |
| 2002/0091116 | A1 | 7/2002 | Zhu et al. |
| 2003/0092095 | A1 | 5/2003 | Huang |
| 2003/0149001 | A1 | 8/2003 | Barvian et al. |
| 2004/0087798 | A1 | 5/2004 | Yamada |
| 2004/0097517 | A1 | 5/2004 | Dwyer et al. |
| 2004/0116399 | A1 | 6/2004 | Zhu et al. |
| 2004/0127523 | A1 | 7/2004 | Bacopoulos et al. |
| 2004/0204339 | A1 | 10/2004 | DiMartino |
| 2004/0214870 | A1 | 10/2004 | Xin et al. |
| 2005/0054850 | A1 | 3/2005 | Wu et al. |
| 2005/0119305 | A1 | 6/2005 | Naka et al. |
| 2005/0260277 | A1 | 11/2005 | Giles |
| 2006/0084691 | A1 | 4/2006 | Piperdi |
| 2006/0194843 | A1 | 8/2006 | Berdini et al. |
| 2008/0139620 | A1 | 6/2008 | Wyatt et al. |
| 2008/0161251 | A1 | 7/2008 | Curry et al. |
| 2008/0161355 | A1 | 7/2008 | Curry et al. |
| 2008/0194562 | A1 | 8/2008 | Wyatt et al. |
| 2008/0200509 | A1 | 8/2008 | Berdini et al. |
| 2008/0269207 | A1 | 10/2008 | Berdini et al. |
| 2008/0306069 | A1 | 12/2008 | Wyatt et al. |
| 2009/0012124 | A1 | 1/2009 | Wyatt et al. |
| 2009/0036435 | A1 | 2/2009 | Curry et al. |
| 2010/0179145 | A1 | 7/2010 | Gallagher et al. |
| 2011/0002879 | A1 | 1/2011 | Curry et al. |
| 2011/0003799 | A1 | 1/2011 | Berdini et al. |
| 2011/0159111 | A1 | 6/2011 | Curry et al. |

FOREIGN PATENT DOCUMENTS

| | | |
|---|---|---|
| EP | 0100172 B1 | 12/1987 |
| EP | 0289879 A1 | 11/1988 |
| EP | 0492125 A1 | 7/1992 |
| EP | 0538231 A1 | 4/1993 |
| EP | 0947500 A1 | 10/1999 |
| EP | 1020471 A1 | 7/2000 |
| EP | 1348707 A1 | 10/2003 |
| EP | 1642594 A1 | 4/2006 |

(Continued)

OTHER PUBLICATIONS

USSN 2011/289,373 Berdini et al, Apr. 11, 2011.*
Voskoglou-Nomikos, Theodora, et al., "Clinical Predictive value of the in Vitro Cell Line, Human Xenograft and Mouse Allograft Preclininical Cancer Models", Clinical Cancer Research, 2003, pp. 4227-4239.
Wyatt, Paul G., et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design", J. Med. Chem., 2008, vol. 51, pp. 4986-4999.

(Continued)

*Primary Examiner* — Andrew D Kosar
*Assistant Examiner* — Raymond Covington
(74) *Attorney, Agent, or Firm* — Heslin Rothenberg Farley & Mesiti P.C.

(57) ABSTRACT

The invention provides an acid addition salt of 4-(2,6-dichloro-benzoylamino)-1H-pyrazole-3-carboxylic acid piperidin-4-ylamide and crystals thereof, the salt being formed with an acid selected from methanesulphonic acid and acetic acid and mixtures thereof.

Also provided are the novel uses of salts of 4-(2,6-dichloro-benzoylamino)-1H-pyrazole-3-carboxylic acid piperidin-4-ylamide, processes for the preparation of 4-(2,6-dichloro-benzoylamino)-1H-pyrazole-3-carboxylic acid piperidin-4-ylamide and its salts and novel chemical intermediates.

16 Claims, No Drawings

FOREIGN PATENT DOCUMENTS

| | | |
|---|---|---|
| EP | 1847531 A1 | 10/2007 |
| GB | 1354939 | 5/1974 |
| WO | 94/11026 A2 | 5/1994 |
| WO | 94/13643 A1 | 6/1994 |
| WO | 96/14843 | 5/1996 |
| WO | 97/19052 A1 | 5/1997 |
| WO | 97/19062 A1 | 5/1997 |
| WO | 97/36585 A1 | 10/1997 |
| WO | 97/36881 A1 | 10/1997 |
| WO | 97/36897 A1 | 10/1997 |
| WO | 97/41824 A2 | 11/1997 |
| WO | 97/48672 A2 | 12/1997 |
| WO | 98/28269 A1 | 7/1998 |
| WO | 98/49166 A1 | 11/1998 |
| WO | 98/52941 A1 | 11/1998 |
| WO | 98/57937 A2 | 12/1998 |
| WO | 99/32454 A1 | 7/1999 |
| WO | 99/32477 A1 | 7/1999 |
| WO | 99/67235 A1 | 12/1999 |
| WO | 00/39108 A1 | 7/2000 |
| WO | 00/59902 A2 | 10/2000 |
| WO | 00/62778 A1 | 10/2000 |
| WO | 00/68191 A1 | 11/2000 |
| WO | 00/71516 A2 | 11/2000 |
| WO | 01/02369 A2 | 1/2001 |
| WO | 01/02385 A1 | 1/2001 |
| WO | 01/14331 A2 | 3/2001 |
| WO | 01/19788 A2 | 3/2001 |
| WO | 01/19798 A2 | 3/2001 |
| WO | 01/51653 A1 | 7/2001 |
| WO | 01/53274 A1 | 7/2001 |
| WO | 01/58869 A2 | 8/2001 |
| WO | 01/64642 A2 | 9/2001 |
| WO | 01/64643 A2 | 9/2001 |
| WO | 01/81316 A2 | 11/2001 |
| WO | 01/81345 A1 | 11/2001 |
| WO | 01/98290 A2 | 12/2001 |
| WO | 02/00651 A2 | 1/2002 |
| WO | 02/10146 A1 | 2/2002 |
| WO | 02/18346 A1 | 3/2002 |
| WO | 02/22601 A1 | 3/2002 |
| WO | 02/22603 A1 | 3/2002 |
| WO | 02/22605 A1 | 3/2002 |
| WO | 02/22608 A1 | 3/2002 |
| WO | 02/34721 A1 | 5/2002 |
| WO | 02/50065 A2 | 6/2002 |
| WO | 02/051810 A2 | 7/2002 |
| WO | 02/059111 A2 | 8/2002 |
| WO | 02/062804 A1 | 8/2002 |
| WO | 02/064586 A2 | 8/2002 |
| WO | 02/066470 A1 | 8/2002 |
| WO | 02/068406 A2 | 9/2002 |
| WO | 02/070483 A1 | 9/2002 |
| WO | 02/074312 A1 | 9/2002 |
| WO | 02/074774 A1 | 9/2002 |
| WO | 02/083624 A1 | 10/2002 |
| WO | 02/094183 A2 | 11/2002 |
| WO | 02/094791 A1 | 11/2002 |
| WO | 02/101007 A2 | 12/2002 |
| WO | 03/011287 A1 | 2/2003 |
| WO | 03/018536 A1 | 3/2003 |
| WO | 03/020217 A2 | 3/2003 |
| WO | 03/024448 A2 | 3/2003 |
| WO | 03/037899 A1 | 5/2003 |
| WO | 03/040147 A1 | 5/2003 |
| WO | 03/048081 A2 | 6/2003 |
| WO | 03/048158 A1 | 6/2003 |
| WO | 03/068767 A1 | 8/2003 |
| WO | 03/077918 A1 | 9/2003 |
| WO | 03/082872 A1 | 10/2003 |
| WO | 03/101953 A2 | 12/2003 |
| WO | 2004/000318 A2 | 12/2003 |
| WO | 2004/014864 A1 | 2/2004 |
| WO | 2004/039795 A2 | 5/2004 |
| WO | 2004/060306 A1 | 7/2004 |
| WO | 2004/085385 A2 | 10/2004 |
| WO | 2004/099127 A1 | 11/2004 |
| WO | 2004/099148 A1 | 11/2004 |
| WO | 2004/110381 A2 | 12/2004 |
| WO | 2005/000309 A2 | 1/2005 |
| WO | 2005/002552 A2 | 1/2005 |
| WO | 2005/012256 A1 | 2/2005 |
| WO | 2005/058881 A1 | 6/2005 |
| WO | 2005/082340 A2 | 9/2005 |
| WO | 2005/087724 A2 | 9/2005 |
| WO | 2006/014290 A2 | 2/2006 |
| WO | 2007/003962 A2 | 1/2007 |
| WO | 2007/129062 A1 | 11/2007 |
| WO | 2007/129066 A1 | 11/2007 |
| WO | 2008/001101 A2 | 1/2008 |
| WO | 2008/007113 A2 | 1/2008 |
| WO | 2008/007122 A2 | 1/2008 |
| WO | 2008/007123 A2 | 1/2008 |
| WO | 2008/009954 A1 | 1/2008 |
| WO | 2008/044041 A1 | 4/2008 |

OTHER PUBLICATIONS

Squires, Matthew S., et al., "Biological characterization of AT7519, a small-molecule inhibitor of cyclin-dependent kinases, in human tumor cell lines", Mol. Cancer Ther., 2009, vol. 8(2), pp. 324-332.

Vippagunta, Sudha R., et al., "Crystalline solids", Advanced Drug Delivery Reviews, 2001, vol. 48, pp. 3-26.

Patani, George A., et al., "Bioisosterism: A Rational Approach in Drug Design", Chem. Rev. 1996, vol. 96, pp. 3147-3176.

Zips, Daniel, et al., "New Anticancer Agents: In Vitro and In Vivo Evaluation", In vivo, 2005, vol. 19, p. 1-7.

Kislyi, V. P., et al. "Hydrogenation of Granular Palladium-containing Catalysts: II. Hydrogenation of Nitroheterocyclic Compounds", Russian Journal of Organic Chemistry 2002, vol. 38, No. 2, pp. 269-271 (Translation of Zhurnal Organicheskoi Khimii (2002), 38(2), 290-293).

Jordan, V. Craig, "Tamoxifen: A Most Unlikely Pioneering Medicine", Nature Reviews: Drug Discovery, 2003, vol. 2, p. 205-213.

Dorwald, F. Zaragoza, "Side Reactions in Organic Synthesis: A Guide to Successful Synthesis Design", 2005, Wiley, Preface.

Wolff, Manfred E., Editor, "Burger's Medicinal Chemistry and Drug Discovery", Wiley, 1996, Fifth Edition, vol. 1, pp. 975-977.

Beers, Mark H., et al., Editors, "The Merck Manual of Diagnosis and Therapy", Seventeenth Edition, published 1999 by Merck Research Laboratories, pp. 397, 398, 948, 949, 973-979, 989-995, 1916, and 1979-1981.

Jain, N. K., et al., "Polymorphism in Pharmacy", Indian Drugs, 1986, vol. 23, No. 6, pp. 315-329.

Braga, Dario, et al., "Making crystals from crystals: a green route to crystal engineering and polymorphism", Chemical Communications, 2005, pp. 3635-3645.

Lieberman Herbert A., et al., Editors, "Pharmaceutical Dosage Forms", published 1980 by Marcel Dekker, Inc., vol. 2, pp. 462-472.

Silverman, Richard B., "The Organic Chemistry of Drug Design and Drug Action" published by Academic Press, 1992, pp. 4-47.

Peckham, Michael, et al., Editors, "The Oxford Textbook of Oncology", published by Oxford University Press, 1995, pp. 447-453.

"STN Database Descriptions", 2006 chemical abstracts catalog, published 2006 by Chemical Abstracts Service, p. 52.

"Miriam Websters Collegiate Dictionary", Tenth Edition (1998).

Ciddi, V., et al, "Elicitation of Taxus sp. cell cultures for production of taxol", Biotechnol. Lett. 1995, 17(12), 1343-6.

STN CAPLUS, Feb. 19, 1996, XP002125277.

Qu G., et al., "Gemcitabine and Targeted Therapy in Metastatic Breast Cancer" Seminars in Oncology, vol. 29, No. 3, Suppl 11, Jun. 2002, pp. 44-52.

Rakhit, A., et al., "Lack of Pharmacokinetic Interaction Between Erlotinib, Docetaxel and Capecitabine in Breast Cancer Patients" European Journal of Cancer. Supplement, Pergamon, Oxford, GB, vol. 1, No. 5, Sep. 2003, p. S115.

Widemann. B. C., et al., "Pediatric phase I trial and pharmacokinetic study of 'Tomudex' (Ralitrexed)" European Journal of Cancer, vol. 35, Sep. 1999, p. S287.

Lindauer, M., et al., "Interferon-Alpha Combined With Cytarabine in Chronic Myelogenous Leukemia—Clinical Benefits" Leukemia and Lymphoma, vol. 41, No. 5/6, 2001, pp. 523-533.

Verweij, J., et al., "Phase II studies of docetaxel in the treatment of various solid tumours" European Journal of Cancer, vol. 31, No. 1004, Oct. 1995, pp. S21-S24.

Xiong, Henry Q., et al., "Cetuximab, A Monoclonal Antibody Targeting the Epidermal Growth Factor Receptor, in Combination With Gemcitabine for Advanced Pancreatic Cancer: A Multicenter Phase II Trial" Journal of Clinical Oncology, vol. 22, No. 13, Jul. 1, 2004, pp. 2610-2616.

Laissue, Jean A., et al., "Survival of Tumor-Bearing Mice Exposed to Heavy Water or Heavy Water Plus Methotrexate" Cancer Research, vol. 42, Mar. 1982, pp. 1125-1129.

Delord, J.P., et al., "A Phase IB Dose-Escalation Trial of Erlotinib, Capecitabine and Oxaliplatin in Metastatic Colorectal Cancer (MCRC) Patients" Program/Proceedings—American Society of Clinical Oncology, The Society, US, vol. 23, 2004, p. 266, ABSTRNO3585.

Mayor, S., "Pemetrexed improves survival in mesothelioma" The Lancet Oncology, vol. 3, No. 7, Jul. 2002, p. 386.

Lynch, Thomas J., et al., "Activating mutations in the epidermal growth factor receptor underlying responsiveness of non-small-cell lung cancer to gefitinib" New England Journal of Medicine, vol. 350, No. 21, May 20, 2004, pp. 2129-2139.

Stone, R., et al., "Skin Reactions to Imatinib Mesylate (STI-571) in Patients With Chronic Myeloid Leukemia (CML): Clinical Features and Histopathology" Blood, vol. 98, No. 11, Part 1, Nov. 16, 2001, p. 141A.

Takahashi, M., et al., "Metastatic Breast Cancer of HER2 Scored 2+ by IHC and HER2 Gene Amplification Assayed by Fish Has a Good Response to Single Agent Therapy With Trastuzumab: A Case Report" Breast Cancer, vol. 10, No. 2, Apr. 2003, pp. 170-174.

Yang, J. C., et al., "A Randomized Trial of Bevacizumab, An Anti-Vascular Endothelial Growth Factor Antibody, for Metastatic Renal Cancer" New England Journal of Medicine, vol. 349, No. 5, Jul. 31, 2003, pp. 427-434.

Cortesi, R., et al. "Formulation study for the antitumor drug camptothecin: liposomes, micellar solutions and a microemulsion" International Journal of Pharmaceutics, vol. 159, 1997, pp. 95-103.

Hardman, W. E., et al., "Efficacy of Treatment of Colon, Lung and Breast Human Carcinoma Xenograft With: Doxorubicin, Cisplatin, Irinotecan or Topotecan" Anticancer Research, vol. 19, 1999, pp. 2269-2274.

Kriegmair, et al., "Interferon-alpha and vinblastine versus medroxyprogesteronacetat in the treatment of metastatic renal cell carcinoma" European Journal of Cancer, Pergamon Press, Oxford, GB, vol. 31, No. 1003, Oct. 1995, p. S35.

Kantarran, H. M., et al., "Experience With Vincristine, Doxorubicin, and Dexamethasone (VAD) Chemotherapy in Adults With Refractory Acute Lymphocytic Leukemia" Cancer, vol. 64, No. 1, Jul. 1, 1989, pp. 16-22.

Bayes, M., et al. "Gateways to Clinical Trials" Methods and Findings in Experimental and Clinical Pharmacology, vol. 26, No. 2, Mar. 2004, pp. 129- 161.

Jekunen, A. P., et al., "Modulation of Cisplatin Cytotoxicity by Permeabilization of the Plasma Membrane by Digitonin in Vitro" Biochemical Pharmacology, vol. 45, No. 10, 1993, pp. 2079-2085.

Blesing, C. H., et al., "Fractionated TBI with idarubicin and cyclophosphamide prior to paediatric allogeneic bone marrow transplant, Early outcome and toxicity" Radiotherapy and Oncology, vol. 40, 1996, p. S36.

Giannios, J., et al., "Antisense chemoradioimmunotherapy consisting of anti-HER-2 scFv linked to high-energy radioisotopes, vinorelbine and 21-nucleotide double-stranded siRNA targeted to DNMT1 induce apoptosis in metastatic breast Ca characterised by hypermethylated oncosuppressor BRCA1 promoter CpG islands an" Radiotherapy and Oncology, vol. 73, Oct. 2004, p. S370, 869 poster.

Yalowich, J.C., et al., "Teniposide (VM-26)- and Etoposide (VP-16-213)-Induced Augmentation of Methotrexate Transport and Polyglutamylation in Ehrlich Ascites Tumor Cells In Vitro" Cancer Research, vol. 42, 1982, pp. 3648-3653.

Edan, C., et al., "Demonstration of the efficacy of mitoxantrone (MTX) using MRI in MS patients with a very active disease" Journal of Neuroimmunology, Elsevier Science Publishers BV, XX, vol. 56-63, 1995, p. 16.

Soldan, M., et al., "Metabolic Inactivation and Efflux of Daunorubicin as Complementary Mechanisms in Tumor Cell Resistance" Advances in Experimental Medicine and Biology, vol. 414, 1997, pp. 537-544.

Konecny, G., et al., "Adjuvant high dose epirubicin and cyclophosphamide with G-CSF support in patients with locally advanced breast cancer" European Journal of Cancer, vol. 31, No. 1003, Oct. 1995, p. S36.

Retzloff, et al., "GnRH antagonist compares favorably, but is not superior, to GnRH agonist microflare for poor responders in IVF." Fertility and Sterility, vol. 80, No. S3, Sep. 2003, pp. S189-S189.

Emanuel, et al., "Inhibition of human tumor xenograft growth by a novel, potent and selective CDK inhibitor" Proceedings of the American Association for Cancer Research Annual Meeting, vol. 44, Jul. 2003, pp. 135-136.

Mazucco R., et al., "American Association for Cancer Research— 93rd Annual Meeting. Immunotherapy, chemoprevention and angiogenesis. Apr. 6-10, 2002, San Francisco, CA, USA." IDRUGS : The Investigational Drugs Journal, vol. 5, No. 5, Apr. 2002, pp. 408-411.

Saito R., et al., "Convection-Enhanced Delivery of Tumor Necrosis Factor-Related Apoptosis-Inducing Ligand With Systemic Administration of Temozolomide Prolongs Survival in an Intracranial Glioblastoma Xenograft Model" Cancer Research, vol. 64, No. 19, Oct. 1, 2004, pp. 6858-6862.

Wong, et al., "Phase II study of two-weekly temozolomide in patients with high-grade gliomas" Journal of Clinical Neuroscience, vol. 13, No. 1, Jan. 2006, pp. 18-22.

Misra, et al., "N-(cycloalkylamino)acyl-2-aminothiazole inhibitors of cyclin-dependent kinase 2. N-[5-[[[5-(1,1-dimethylethyl)-2-oxazolyl]m ethyl]thio]-2-thi azolyl]-4—piperidinecarboxamide (BMS-387032), a highly efficacious and selective antitumor agent" Journal of Medicinal Chemistry, vol. 47, No. 7, Mar. 25, 2004, pp. 1719-1728.

Handrick, R., et al., "Effects of celecoxib and irradiation treatment on prostate cancer cell lines" European Journal of Cancer. Supplement, vol. 2, No. 8, Sep. 2004, p. 196, poster 651.

Takigawa, N., et al. "Modulation of DNA damage induced apoptosis by the proteasome inhibitor bortezomib (PS) in human colorectal and non-small cell lung cancer cells is p53-dependent and NK-kB-independent" European Journal of Cancer. Supplement, vol. 2, No. 8, Sep. 2004, p. 63, poster 203.

Bischoff, et al., "Tamoxifen resistance: the RXR-selective ligand LGD1069 causes complete regression of tamoxifen-resistant mammary carcinoma" Proceedings of the Annual Meeting of the American Association for Cancer Research, New York, NY, US, vol. 40, Mar. 1999, p. 309.

Teixeira, M., et al., "Temozolamide (TMZ) in second-line treatment after pcv in glioblastoma multiforme (GBM). Experience from a single Portuguese institution" European Journal of Cancer, vol. 37, Apr. 2001, p. S344.

Campbell, D. A., et al., "Molecular Pathology in Oncology—The Astrazeneca Perspective" Pharmacogenomics, vol. 5, No. 8, 2004, pp. 1167-1173.

Grant, S., "Targeted Therapies in Cancer" IDRUGS, Current Drugs Ltd, vol. 6, No. 10, 2003, pp. 946-948.

Kristeleit, R., et al., "Histone Modification Enzymes: Novel Targets for Cancer Drugs" Expert Opinion on Emerging Drugs, vol. 9, No. 1, 2004, pp. 135-154.

Byrn, et al., Solid State chemistry of drugs, 2d, Chapters 10 & 11.

Mashkovskii, M., Lekarstvennye sredstva (Medicinal Drugs) Moscow, Novaya Volna, (2001) p. 11 (in Russian).

Pokrovskij, Kratkaja medicinskaja enciklopeclija, M oscow, Nauchno-prakiceskoe obedinenie "Medicinskaja enciklopedija", "Kron-press", 1994, vol. II, pp. 49-50, incompatibility of medicaments (in Russian).

GB search report GB 0501475.8 filed Jan. 22, 2005.

International Search Report PCT/GB2006/000207 filed Jan. 20, 2006.

* cited by examiner

4-(2,6-DICHLORO-BENZOYLAMINO)-1H-PYRAZOLE-3-CARBOXYLIC ACID PIPERIDIN-4-YLAMIDE ACID ADDITION SALTS AS KINASE INHIBITORS

CROSS REFERENCE TO RELATED APPLICATIONS

This application is a continuation of U.S. application Ser. No. 11/814,458 (published as US 2009-0012124 A1 on Jan. 8, 2009), which is a national phase filing under 35 U.S.C. §371 of PCT International Application No. PCT/GB2006/000207, filed Jan. 20, 2006, and published under PCT Article 21(2) in English as WO 2006/077426 on Jul. 27, 2006. PCT/GB2006/000207 claimed priority from British Application No. 0501475.8, filed Jan. 22, 2005, and U.S. Application No. 60/645,973, filed Jan. 21, 2005. The entire contents of each of the prior applications are incorporated herein by reference.

FIELD OF THE INVENTION

This invention relates to acid addition salts of the compound 4-(2,6-dichloro-benzoylamino)-1H-pyrazole-3-carboxylic acid piperidin-4-ylamide and crystalline forms thereof, processes for preparing the compound and its acid addition salts, novel chemical intermediates for use in the processes, and therapeutic uses of the compound and its acid addition salts. The invention also relates to novel therapeutic uses of 4-(2,6-dichloro-benzoylamino)-1H-pyrazole-3-carboxylic acid piperidin-4-ylamide and analogues thereof.

BACKGROUND OF THE INVENTION

The compound 4-(2,6-dichloro-benzoylamino)-1H-pyrazole-3-carboxylic acid piperidin-4-ylamide and the hydrochloric acid addition salt thereof are disclosed in our earlier International patent application number PCT/GB2004/003179 (Publication No. WO 2005/012256) as being inhibitors of Cyclin Dependent Kinases (CDK kinases) and Glycogen Synthase Kinase-3 (GSK3).

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

Cyclin Dependent Kinases

The process of eukaryotic cell division may be broadly divided into a series of sequential phases termed G1, S, G2 and M. Correct progression through the various phases of the cell cycle has been shown to be critically dependent upon the spatial and temporal regulation of a family of proteins known as cyclin dependent kinases (cdks) and a diverse set of their cognate protein partners termed cyclins. Cdks are cdc2 (also known as cdk1) homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific cdk partner proteins.

Modulation of the expression levels, degradation rates, and activation levels of various cdks and cyclins throughout the cell cycle leads to the cyclical formation of a series of cdk/cyclin complexes, in which the cdks are enzymatically active. The formation of these complexes controls passage through discrete cell cycle checkpoints and thereby enables the process of cell division to continue. Failure to satisfy the prerequisite biochemical criteria at a given cell cycle checkpoint, i.e. failure to form a required cdk/cyclin complex, can lead to cell cycle arrest and/or cellular apoptosis. Aberrant cellular proliferation, as manifested in cancer, can often be attributed to loss of correct cell cycle control. Inhibition of cdk enzymatic activity therefore provides a means by which abnormally dividing cells can have their division arrested and/or be killed. The diversity of cdks, and cdk complexes, and their critical roles in mediating the cell cycle, provides a broad spectrum of potential therapeutic targets selected on the basis of a defined biochemical rationale.

Progression from the G1 phase to the S phase of the cell cycle is primarily regulated by cdk2, cdk3, cdk4 and cdk6 via association with members of the D and E type cyclins. The D-type cyclins appear instrumental in enabling passage beyond the G1 restriction point, where as the cdk2/cyclin E complex is key to the transition from the G1 to S phase. Subsequent progression through S phase and entry into G2 is thought to require the cdk2/cyclin A complex. Both mitosis, and the G2 to M phase transition which triggers it, are regulated by complexes of cdk1 and the A and B type cyclins.

During G1 phase Retinoblastoma protein (Rb), and related pocket proteins such as p130, are substrates for cdk(2, 4, & 6)/cyclin complexes. Progression through G1 is in part facilitated by hyperphosphorylation, and thus inactivation, of Rb and p130 by the cdk(4/6)/cyclin-D complexes. Hyperphosphorylation of Rb and p130 causes the release of transcription factors, such as E2F, and thus the expression of genes necessary for progression through G1 and for entry into S-phase, such as the gene for cyclin E. Expression of cyclin E facilitates formation of the cdk2/cyclin E complex which amplifies, or maintains, E2F levels via further phosphorylation of Rb. The cdk2/cyclin E complex also phosphorylates other proteins necessary for DNA replication, such as NPAT, which has been implicated in histone biosynthesis. G1 progression and the G1/S transition are also regulated via the mitogen stimulated Myc pathway, which feeds into the cdk2/cyclin E pathway. Cdk2 is also connected to the p53 mediated DNA damage response pathway via p53 regulation of p21 levels. p21 is a protein inhibitor of cdk2/cyclin E and is thus capable of blocking, or delaying, the G1/S transition. The cdk2/cyclin E complex may thus represent a point at which biochemical stimuli from the Rb, Myc and p53 pathways are to some degree integrated. Cdk2 and/or the cdk2/cyclin E complex therefore represent good targets for therapeutics designed at arresting, or recovering control of, the cell cycle in aberrantly dividing cells.

The exact role of cdk3 in the cell cycle is not clear. As yet no cognate cyclin partner has been identified, but a dominant negative form of cdk3 delayed cells in G1, thereby suggesting that cdk3 has a role in regulating the G1/S transition.

Although most cdks have been implicated in regulation of the cell cycle there is evidence that certain members of the cdk family are involved in other biochemical processes. This is exemplified by cdk5 which is necessary for correct neuronal development and which has also been implicated in the phosphorylation of several neuronal proteins such as Tau, NUDE-1, synapsin1, DARPP32 and the Munc18/Syntaxin1A complex. Neuronal cdk5 is conventionally activated by binding to the p35/p39 proteins. Cdk5 activity can, however, be deregulated by the binding of p25, a truncated version of p35. Conversion of p35 to p25, and subsequent deregulation of cdk5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

Cdk7 is a nuclear protein that has cdc2 CAK activity and binds to cyclin H. Cdk7 has been identified as component of the TFIIH transcriptional complex which has RNA polymerase II C-terminal domain (CTD) activity. This has been associated with the regulation of HIV-1 transcription via a Tat-mediated biochemical pathway. Cdk8 binds cyclin C and has been implicated in the phosphorylation of the CTD of RNA polymerase II. Similarly the cdk9/cyclin-T1 complex (P-TEFb complex) has been implicated in elongation control of RNA polymerase II. PTEF-b is also required for activation of transcription of the HIV-1 genome by the viral transactivator Tat through its interaction with cyclin T1. Cdk7, cdk8, cdk9 and the P-TEFb complex are therefore potential targets for anti-viral therapeutics.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as wee1, Myt1 and Mik1. Dephosphorylation is performed by phosphatases such as cdc25(a & c), pp2a, or KAP.

Cdk/cyclin complex activity may be further regulated by two families of endogenous cellular proteinaceous inhibitors: the Kip/Cip family, or the INK family. The INK proteins specifically bind cdk4 and cdk6. p16$^{ink4}$ (also known as MTS1) is a potential tumour suppressor gene that is mutated, or deleted, in a large number of primary cancers. The Kip/Cip family contains proteins such as p21$^{Cip1,Waf1}$, p27$^{Kip1}$ and p57$^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumour agents as they would not directly interact with DNA and should therefore reduce the risk of secondary tumour development.

Glycogen Synthase Kinase

Glycogen Synthase Kinase-3 (GSK3) is a serine-threonine kinase that occurs as two ubiquitously expressed isoforms in humans (GSK3α & beta GSK3β). GSK3 has been implicated as having roles in embryonic development, protein synthesis, cell proliferation, cell differentiation, microtubule dynamics, cell motility and cellular apoptosis. As such GSK3 has been implicated in the progression of disease states such as diabetes, cancer, Alzheimer's disease, stroke, epilepsy, motor neuron disease and/or head trauma. Phylogenetically GSK3 is most closely related to the cyclin dependent kinases (CDKs).

The consensus peptide substrate sequence recognised by GSK3 is (Ser/Thr)-X-X-X-(pSer/pThr), where X is any amino acid (at positions (n+1), (n+2), (n+3)) and pSer and pThr are phospho-serine and phospho-threonine respectively (n+4). GSK3 phosphorylates the first serine, or threonine, at position (n). Phospho-serine, or phospho-threonine, at the (n+4) position appears necessary for priming GSK3 to give maximal substrate turnover. Phosphorylation of GSK3α at Ser21, or GSK3β at Ser9, leads to inhibition of GSK3. Mutagenesis and peptide competition studies have led to the model that the phosphorylated N-terminus of GSK3 is able to compete with phospho-peptide substrate (S/TXXXpS/pT) via an autoinhibitory mechanism. There are also data suggesting that GSK3α and GSKβ may be subtly regulated by phosphorylation of tyrosines 279 and 216 respectively. Mutation of these residues to a Phe caused a reduction in in vivo kinase activity. The X-ray crystallographic structure of GSK3β has helped to shed light on all aspects of GSK3 activation and regulation.

GSK3 forms part of the mammalian insulin response pathway and is able to phosphorylate, and thereby inactivate, glycogen synthase. Upregulation of glycogen synthase activity, and thereby glycogen synthesis, through inhibition of GSK3, has thus been considered a potential means of combating type II, or non-insulin-dependent diabetes mellitus (NIDDM): a condition in which body tissues become resistant to insulin stimulation. The cellular insulin response in liver, adipose, or muscle tissues is triggered by insulin binding to an extracellular insulin receptor. This causes the phosphorylation, and subsequent recruitment to the plasma membrane, of the insulin receptor substrate (IRS) proteins. Further phosphorylation of the IRS proteins initiates recruitment of phosphoinositide-3 kinase (PI3K) to the plasma membrane where it is able to liberate the second messenger phosphatidylinosityl 3,4,5-trisphosphate (PIP3). This facilitates co-localisation of 3-phosphoinositide-dependent protein kinase 1 (PDK1) and protein kinase B (PKB or Akt) to the membrane, where PDK1 activates PKB. PKB is able to phosphorylate, and thereby inhibit, GSK3α and/or GSKβ through phosphorylation of Ser9, or ser21, respectively. The inhibition of GSK3 then triggers upregulation of glycogen synthase activity. Therapeutic agents able to inhibit GSK3 may thus be able to induce cellular responses akin to those seen on insulin stimulation. A further in vivo substrate of GSK3 is the eukaryotic protein synthesis initiation factor 2B (eIF2B). eIF2B is inactivated via phosphorylation and is thus able to suppress protein biosynthesis. Inhibition of GSK3, e.g. by inactivation of the "mammalian target of rapamycin" protein (mTOR), can thus upregulate protein biosynthesis. Finally there is some evidence for regulation of GSK3 activity via the mitogen activated protein kinase (MAPK) pathway through phosphorylation of GSK3 by kinases such as mitogen activated protein kinase activated protein kinase 1 (MAPKAP-K1 or RSK). These data suggest that GSK3 activity may be modulated by mitogenic, insulin and/or amino acid stimuli.

It has also been shown that GSK3β is a key component in the vertebrate Wnt signalling pathway. This biochemical pathway has been shown to be critical for normal embryonic development and regulates cell proliferation in normal tissues. GSK3 becomes inhibited in response to Wnt stimuli. This can lead to the de-phosphorylation of GSK3 substrates such as Axin, the adenomatous polyposis coli (APC) gene product and β-catenin. Aberrant regulation of the Wnt pathway has been associated with many cancers. Mutations in APC, and/or β-catenin, are common in colorectal cancer and other tumours. β-catenin has also been shown to be of importance in cell adhesion. Thus GSK3 may also modulate cellular adhesion processes to some degree. Apart from the biochemical pathways already described there are also data implicating GSK3 in the regulation of cell division via phosphorylation of cyclin-D1, in the phosphorylation of transcription factors such as c-Jun, CCAAT/enhancer binding protein α (C/EBPα), c-Myc and/or other substrates such as Nuclear Factor of Activated T-cells (NFATc), Heat Shock Factor-1 (HSF-1) and the c-AMP response element binding protein (CREB). GSK3 also appears to play a role, albeit tissue specific, in regulating cellular apoptosis. The role of GSK3 in modulating cellular apoptosis, via a pro-apoptotic mechanism, may be of particular relevance to medical conditions in which neuronal apoptosis can occur. Examples of these are head trauma, stroke, epilepsy, Alzheimer's and motor neuron diseases, progressive supranuclear palsy, corticobasal degeneration, and Pick's disease. In vitro it has been shown that GSK3 is able to hyper-phosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhibition of Tau phosphorylation, through inhibition of GSK3, may thus provide a means of limiting and/or preventing neurodegenerative effects.

Diffuse Large B-Cell Lymphomas (DLBCL)

Cell cycle progression is regulated by the combined action of cyclins, cyclin-dependent kinases (CDKs), and CDK-inhibitors (CDKi), which are negative cell cycle regulators. p27KIP1 is a CDKi key in cell cycle regulation, whose degradation is required for G1/S transition. In spite of the absence of p27KIP1 expression in proliferating lymphocytes, some aggressive B-cell lymphomas have been reported to show an anomalous p27KIP1 staining. An abnormally high expression of p27KIP1 was found in lymphomas of this type. Analysis of the clinical relevance of these findings showed that a high level of p27KIP1 expression in this type of tumour is an adverse prognostic marker, in both univariate and multivariate analysis. These results show that there is abnormal p27KIP1 expression in Diffuse Large B-cell Lymphomas (DLBCL), with adverse clinical significance, suggesting that this anomalous p27KIP1 protein may be rendered non-functional through interaction with other cell cycle regulator proteins. (Br. J. Cancer. 1999 July; 80(9):1427-34. p27KIP1 is abnormally expressed in Diffuse Large B-cell Lymphomas and is associated with an adverse clinical outcome. Saez A, Sanchez E, Sanchez-Beato M, Cruz M A, Chacon I, Munoz E, Camacho F I, Martinez-Montero J C, Mollejo M, Garcia J F, Piris M A. Department of Pathology, Virgen de la Salud Hospital, Toledo, Spain.)

Chronic Lymphocytic Leukemia

B-Cell chronic lymphocytic leukaemia (CLL) is the most common leukaemia in the Western hemisphere, with approximately 10,000 new cases diagnosed each year (Parker S L, Tong T, Bolden S, Wingo P A: Cancer statistics, 1997. Ca. Cancer. J. Clin. 47:5, (1997)). Relative to other forms of leukaemia, the overall prognosis of CLL is good, with even the most advanced stage patients having a median survival of 3 years.

The addition of fludarabine as initial therapy for symptomatic CLL patients has led to a higher rate of complete responses (27% v 3%) and duration of progression-free survival (33 v 17 months) as compared with previously used alkylator-based therapies. Although attaining a complete clinical response after therapy is the initial step toward improving survival in CLL, the majority of patients either do not attain complete remission or fail to respond to fludarabine. Furthermore, all patients with CLL treated with fludarabine eventually relapse, making its role as a single agent purely palliative (Rai K R, Peterson B, Elias L, Shepherd L, Hines J, Nelson D, Cheson B, Kolitz J, Schiffer C A: A randomized comparison of fludarabine and chlorambucil for patients with previously untreated chronic lymphocytic leukemia. A CALGB SWOG, CTG/NCI-C and ECOG Inter-Group Study. Blood 88:141a, 1996 (abstr 552, suppl 1). Therefore, identifying new agents with novel mechanisms of action that complement fludarabine's cytotoxicity and abrogate the resistance induced by intrinsic CLL drug-resistance factors will be necessary if further advances in the therapy of this disease are to be realized.

The most extensively studied, uniformly predictive factor for poor response to therapy and inferior survival in CLL patients is aberrant p53 function, as characterized by point mutations or chromosome 17p13 deletions. Indeed, virtually no responses to either alkylator or purine analog therapy have been documented in multiple single institution case series for those CLL patients with abnormal p53 function. Introduction of a therapeutic agent that has the ability to overcome the drug resistance associated with p53 mutation in CLL would potentially be a major advance for the treatment of the disease.

Flavopiridol and CYC 202, inhibitors of cyclin-dependent kinases induce in vitro apoptosis of malignant cells from B-cell chronic lymphocytic leukemia (B-CLL).

Flavopiridol exposure results in the stimulation of caspase 3 activity and in caspase-dependent cleavage of p27(kip1), a negative regulator of the cell cycle, which is overexpressed in B-CLL (Blood. 1998 Nov. 15; 92(10):3804-16 Flavopiridol induces apoptosis in chronic lymphocytic leukemia cells via activation of caspase-3 without evidence of bcl-2 modulation or dependence on functional p53. Byrd J C, Shinn C, Waselenko J K, Fuchs E J, Lehman T A, Nguyen P L, Flinn I W, Diehl L F, Sausville E, Greyer M R).

PRIOR ART

WO 02/34721 from Du Pont discloses a class of indeno[1,2-c]pyrazol-4-ones as inhibitors of cyclin dependent kinases.

WO 01/81348 from Bristol Myers Squibb describes the use of 5-thio-, sulphinyl- and sulphonylpyrazolo[3,4-b]-pyridines as cyclin dependent kinase inhibitors.

WO 00/62778 also from Bristol Myers Squibb discloses a class of protein tyrosine kinase inhibitors.

WO 01/72745A1 from Cyclacel describes 2-substituted 4-heteroaryl-pyrimidines and their preparation, pharmaceutical compositions containing them and their use as inhibitors of cyclin-dependant kinases (CDKs) and hence their use in the treatment of proliferative disorders such as cancer, leukaemia, psoriasis and the like.

WO 99/21845 from Agouron describes 4-aminothiazole derivatives for inhibiting cyclin-dependent kinases (CDKs), such as CDK1, CDK2, CDK4, and CDK6. The invention is also directed to the therapeutic or prophylactic use of pharmaceutical compositions containing such compounds and to methods of treating malignancies and other disorders by administering effective amounts of such compounds.

WO 01/53274 from Agouron discloses as CDK kinase inhibitors a class of compounds which can comprise an amide-substituted benzene ring linked to an N-containing heterocyclic group.

WO 01/98290 (Pharmacia & Upjohn) discloses a class of 3-aminocarbonyl-2-carboxamido thiophene derivatives as protein kinase inhibitors.

WO 01/53268 and WO 01/02369 from Agouron disclose compounds that mediate or inhibit cell proliferation through the inhibition of protein kinases such as cyclin dependent kinase or tyrosine kinase. The Agouron compounds have an aryl or heteroaryl ring attached directly or though a CH=CH or CH=N group to the 3-position of an indazole ring.

WO 00/39108 and WO 02/00651 (both to Du Pont Pharmaceuticals) describe heterocyclic compounds that are inhibitors of trypsin-like serine protease enzymes, especially factor Xa and thrombin. The compounds are stated to be useful as anticoagulants or for the prevention of thromboembolic disorders.

US 2002/0091116 (Zhu et al.), WO 01/19798 and WO 01/64642 each disclose diverse groups of heterocyclic compounds as inhibitors of Factor Xa. Some 1-substituted pyrazole carboxamides are disclosed and exemplified.

U.S. Pat. No. 6,127,382, WO 01/70668, WO 00/68191, WO 97/48672, WO 97/19052 and WO 97/19062 (all to Allergan) each describe compounds having retinoid-like activity for use in the treatment of various hyperproliferative diseases including cancers.

WO 02/070510 (Bayer) describes a class of amino-dicarboxylic acid compounds for use in the treatment of cardiovascular diseases. Although pyrazoles are mentioned generically, there are no specific examples of pyrazoles in this document.

WO 97/03071 (Knoll AG) discloses a class of heterocyclyl-carboxamide derivatives for use in the treatment of central nervous system disorders. Pyrazoles are mentioned generally as examples of heterocyclic groups but no specific pyrazole compounds are disclosed or exemplified.

WO 97/40017 (Novo Nordisk) describes compounds that are modulators of protein tyrosine phosphatases.

WO 03/020217 (Univ. Connecticut) discloses a class of pyrazole 3-carboxamides as cannabinoid receptor modulators for treating neurological conditions. It is stated (page 15) that the compounds can be used in cancer chemotherapy but it is not made clear whether the compounds are active as anti-cancer agents or whether they are administered for other purposes.

WO 01/58869 (Bristol Myers Squibb) discloses cannabinoid receptor modulators that can be used inter alia to treat a variety of diseases. The main use envisaged is the treatment of respiratory diseases, although reference is made to the treatment of cancer.

WO 01/02385 (Aventis Crop Science) discloses 1-(quinoline-4-yl)-1H-pyrazole derivatives as fungicides. 1-Unsubstituted pyrazoles are disclosed as synthetic intermediates.

WO 2004/039795 (Fujisawa) discloses amides containing a 1-substituted pyrazole group as inhibitors of apolipoprotein B secretion. The compounds are stated to be useful in treating such conditions as hyperlipidemia.

WO 2004/000318 (Cellular Genomics) discloses various amino-substituted monocycles as kinase modulators. None of the exemplified compounds are pyrazoles.

SUMMARY OF THE INVENTION

The invention provides inter alia acid addition salts of the compound 4-(2,6-dichloro-benzoylamino)-1H-pyrazole-3-carboxylic acid piperidin-4-ylamide and crystalline forms of the acid addition salts, particularly the methanesulphonic acid and acetic acid salts.

The invention also provides novel processes for preparing the compound, its acid addition salts and crystalline forms thereof, as well as novel chemical intermediates for use in the processes.

The invention further provides therapeutic uses of the compound and its acid addition salts, as well as novel therapeutic uses of analogues of 4-(2,6-dichloro-benzoylamino)-1H-pyrazole-3-carboxylic acid piperidin-4-ylamide.

Accordingly, in a first aspect, the invention provides an acid addition salt of 4-(2,6-dichloro-benzoylamino)-1H-pyrazole-3-carboxylic acid piperidin-4-ylamide, the salt being other than a hydrochloride salt.

The free base of 4-(2,6-dichloro-benzoylamino)-1H-pyrazole-3-carboxylic acid piperidin-4-ylamide from which the salts are derived has the formula (I):

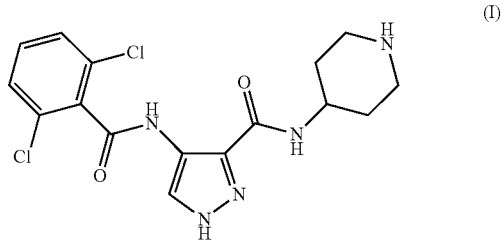

The compound of the formula (I) may be referred to in this application by its chemical name or, for convenience, as "the compound", "the compound of formula (I)" or "the compound of the invention". Each of these synonyms refers to the compound shown in formula (I) above and having the chemical name 4-(2,6-dichloro-benzoylamino)-1H-pyrazole-3-carboxylic acid piperidin-4-ylamide.

The salts to which this application relates are acid addition salts of 4-(2,6-dichloro-benzoylamino)-1H-pyrazole-3-carboxylic acid piperidin-4-ylamide. The terms "salt" and "acid addition salt", may be used interchangeably in this application as may the terms "salts" and "acid addition salts". The terms "salt" and "salts" as used herein refer to the acid addition salts unless the context indicates otherwise.

References to the compound 4-(2,6-dichloro-benzoylamino)-1H-pyrazole-3-carboxylic acid piperidin-4-ylamide and its acid addition salts include within their scope all solvates, tautomers and isotopes thereof and, where the context admits, N-oxides, other ionic forms and prodrugs.

The acid addition salt may be selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

One sub-group of acid addition salts includes salts formed with an acid selected from the group consisting of acetic, adipic, ascorbic (e.g. L-ascorbic), aspartic (e.g. L-aspartic), caproic, carbonic, citric, dodecanoic, fumaric, galactaric, glucoheptonic, gluconic (e.g. D-gluconic), glucuronic (e.g. D-glucuronic), glutamic (e.g. L-glutamic), glycolic, hippuric, lactic (e.g. (+)-L-lactic and (±)-DL-lactic), maleic, palmitic, phosphoric, sebacic, stearic, succinic, sulphuric, tartaric (e.g. (+)-L-tartaric) and thiocyanic acids.

More particularly the salts are acid addition salts formed with an acid selected from methanesulphonic acid and acetic acid, and mixtures thereof.

In one embodiment, the salt is an acid addition salt formed with methanesulphonic acid.

In another embodiment, the salt is an acid addition salt formed with acetic acid.

For convenience the salts formed from methanesulphonic acid and acetic acid may be referred to herein as the methanesulphonate or mesylate salts and acetate salts respectively.

In the solid state, the salts of the invention can be crystalline or amorphous or a mixture thereof.

In one embodiment, the salts are amorphous.

In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

In another embodiment, the salts are substantially crystalline; i.e. they are from 50% to 100% crystalline, and more particularly they may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

In a further embodiment, the salts are selected from the group consisting of salts that are from 50% to 100% crystalline, salts that are at least 50% crystalline, salts that are at least 60% crystalline, salts that are at least 70% crystalline, salts that are at least 80% crystalline, salts that are at least 90% crystalline, salts that are at least 95% crystalline, salts that are at least 98% crystalline, salts that are at least 99% crystalline, salts that are at least 99.5% crystalline, and salts that are at least 99.9% crystalline, for example 100% crystalline.

More preferably the salts may be those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

One example of a substantially crystalline salt is a crystalline salt formed with methanesulphonic acid.

Another example of a substantially crystalline salt is a crystalline salt formed with acetic acid.

The salts of the invention, in the solid state, can be solvated (e.g. hydrated) or non-solvated (e.g. anhydrous).

In one embodiment, the salts are non-solvated (e.g. anhydrous). An example of a non-solvated salt is the crystalline salt formed with methanesulphonic acid as defined herein.

The term "anhydrous" as used herein does not exclude the possibility of the presence of some water on or in the salt (e.g a crystal of the salt). For example, there may be some water present on the surface of the salt (e.g. salt crystal), or minor amounts within the body of the salt (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the salts are solvated. Where the salts are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound.

Other solvates include alcoholates such as ethanolates and isopropanolates.

The salts of the present invention can be synthesized from the parent compound 4-(2,6-dichloro-benzoylamino)-1H-pyrazole-3-carboxylic acid piperidin-4-ylamide by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the parent compound 4-(2,6-dichloro-benzoylamino)-1H-pyrazole-3-carboxylic acid piperidin-4-ylamide with the appropriate acid in water or in an organic solvent, or in a mixture of the two; generally, nonaqueous media such as ether, ethyl acetate, ethanol, isopropanol, or acetonitrile are used.

In another aspect, the invention provides a method of preparing an acid addition salt of 4-(2,6-dichloro-benzoylamino)-1H-pyrazole-3-carboxylic acid piperidin-4-ylamide, which method comprises forming a solution of 4-(2,6-dichloro-benzoylamino)-1H-pyrazole-3-carboxylic acid piperidin-4-ylamide free base in a solvent (typically an organic solvent) or mixture of solvents, and treating the solution with an acid to form a precipitate of the acid addition salt.

The acid may be added as a solution in a solvent which is miscible with the solvent in which the free base is dissolved. The solvent in which the free base is initially dissolved may be one in which the acid addition salt thereof is insoluble. Alternatively, the solvent in which the free base is initially dissolved may be one in which the acid addition salt is at least partially soluble, a different solvent in which the acid addition salt is less soluble subsequently being added such that the salt precipitates out of solution.

In an alternative method of forming an acid addition salt, 4-(2,6-dichloro-benzoylamino)-1H-pyrazole-3-carboxylic acid piperidin-4-ylamide is dissolved in a solvent comprising a volatile acid and optionally a co-solvent, thereby to form a solution of the acid addition salt with the volatile acid, and the resulting solution is then concentrated or evaporated to isolate the salt. An example of an acid addition salt that can be made in this way is the acetate salt.

In another aspect, the invention provides a method of forming an acid addition salt of 4-(2,6-dichloro-benzoylamino)-1H-pyrazole-3-carboxylic acid piperidin-4-ylamide as defined herein, which method comprises treating a compound of the formula (X):

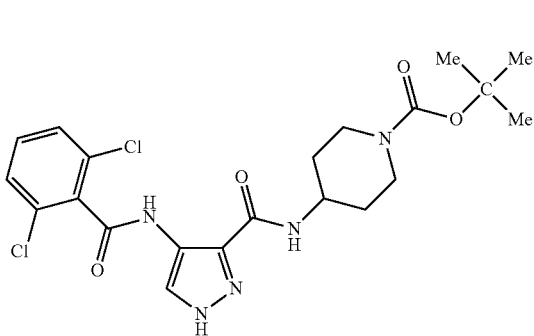

with an organic or inorganic acid as defined herein, other than hydrochloric acid, in an organic solvent to remove the tert-butyloxycarbonyl group and form an acid addition salt of 4-(2,6-dichloro-benzoylamino)-1H-pyrazole-3-carboxylic acid piperidin-4-ylamide with the organic or inorganic acid, and optionally isolating the acid addition salt thus formed.

The salt is typically precipitated from the organic solvent as it is formed and hence can be isolated by separation of the solid from the solution, e.g. by filtration.

One salt form of the invention can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid by one of the methods described above or elsewhere herein.

Salts such as acid addition salts have a number of advantages over the corresponding free base. For example, the salts will enjoy one or more of the following advantages over the free base in that they:
  will be more soluble and hence will be better for i.v. administration (e.g. by infusion)
  will have better stability (e.g. improved shelf life);
  will have better thermal stability;
  will be less basic and therefore better for i.v. administration;
  will have advantages for production;
  will have improved solubility in aqueous solution;
  will have better physicochemical properties;
  may have improved anti-cancer activity; and
  may have an improved therapeutic index.

The methanesulphonate salt form is particularly advantageous because of its good stability at elevated temperatures and in conditions of high relative humidity, its non-hygroscopicity (as defined herein), absence of polymorph and hydrate formation, and stability in aqueous conditions. Moreover, it has excellent water solubility and has better physiochemical properties (such as a high melting point) relative to other salts.

The term 'stable' or 'stability' as used herein includes chemical stability and solid state (physical) stability. The term 'chemical stability' means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition. 'Solid-state stability' means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

The terms "non-hygroscopic" and "non-hygroscopicity" and related terms as used herein refer to substances that absorb less than 5% by weight (relative to their own weight) of water when exposed to conditions of high relative humidity, for example 90% relative humidity, and/or do not undergo changes in crystalline form in conditions of high humidity and/or do not absorb water into the body of the crystal (internal water) in conditions of high relative humidity.

Preferred salts for use in the preparation of liquid (e.g. aqueous) pharmaceutical compositions are acid addition salts (such as the mesylate and acetate and mixtures thereof as defined herein) having a solubility in a given liquid carrier (e.g. water) of greater than 15 mg/ml of the liquid carrier (e.g. water), more typically greater than 20 mg/ml, preferably greater than 25 mg/ml, and more preferably greater than 30 mg/ml.

In another aspect, there is provided a pharmaceutical composition comprising an aqueous solution containing an acid addition salt of 4-(2,6-dichloro-benzoylamino)-1H-pyrazole-3-carboxylic acid piperidin-4-ylamide (such as the mesylate and acetate and mixtures thereof as defined herein, and preferably the mesylate) in a concentration of greater than 15 mg/ml, typically greater than 20 mg/ml, preferably greater than 25 mg/ml, and more preferably greater than 30 mg/ml.

In a preferred embodiment, the pharmaceutical composition comprises an aqueous solution containing an acid addition salt of 4-(2,6-dichloro-benzoylamino)-1H-pyrazole-3-carboxylic acid piperidin-4-ylamide selected from an acetate or methanesulphonate salt or a mixture thereof in a concentration of greater than 15 mg/ml, typically greater than 20 mg/ml, preferably greater than 25 mg/ml, and more preferably greater than 30 mg/ml.

In another aspect, the invention provides an aqueous solution of an acid addition salt of 4-(2,6-dichloro-benzoylamino)-1H-pyrazole-3-carboxylic acid piperidin-4-ylamide (such as the mesylate and acetate and mixtures thereof as defined herein), wherein the aqueous solution has a pH of 2 to 12, for example 2 to 9, and more particularly 4 to 7.

In the aqueous solutions defined above, the acid addition salt may be any of the salts described herein but, in one preferred embodiment, is a mesylate or acetate salt as defined herein, and in particular the mesylate salt.

The invention also provides an aqueous solution of 4-(2,6-dichloro-benzoylamino)-1H-pyrazole-3-carboxylic acid piperidin-4-ylamide in protonated form together with one or more counter ions and optionally one or more further counter ions. In one embodiment one of the counter ions is selected from methanesulphonate and acetate. In another embodiment one of the counter ions is from the formulation buffer as described herein such as acetate. In a further embodiment there may be one or more further counter ions such as a chloride ion (e.g. from saline).

The invention therefore provides an aqueous solution of 4-(2,6-dichloro-benzoylamino)-1H-pyrazole-3-carboxylic acid piperidin-4-ylamide in protonated form together with one or more counter ions selected from methanesulphonate and acetate and optionally one or more further counter ions such as a chloride ion.

In the situation where there is more than one counter ion the aqueous solution of 4-(2,6-dichloro-benzoylamino)-1H-pyrazole-3-carboxylic acid piperidin-4-ylamide in protonated form will potentially contain a mixture of counter ions for example a mixture of methanesulphonate and acetate counter ions and optionally one or more further counter ions such as a chloride ion.

The invention therefore provides an aqueous solution of 4-(2,6-dichloro-benzoylamino)-1H-pyrazole-3-carboxylic acid piperidin-4-ylamide in protonated form together with one or more counter ions selected from methanesulphonate and acetate and optionally one or more further counter ions such as a chloride ion, and a mixture thereof.

The aqueous solutions can be formed inter alia by dissolving a mesylate salt in a solution of acetate ions (e.g an acetate buffer) or by dissolving an acetate salt in a solution of mesylate ions. The mesylate and acetate ions may be present in the solution in a mesylate:acetate ratio of from 10:1 or less, for example 10:1 to 1:10, more preferably less then 8:1, or less than 7:1, or less than 6:1, or less than 5:1 or less than 4:1 or less than 3:1 or less than 2:1 or less than 1:1, more particularly from 1:1 to 1:10. In one embodiment, the mesylate and acetate ions are present in the solution in a mesylate:acetate ratio of from 1:1 to 1:10, for example 1:1 to 1:8, or 1:1 to 1:7 or 1:1 to 1:6 or 1:1 to 1:5, e.g. approximately 1:4.8.

The aqueous solutions of the salts may be buffered or unbuffered but in one embodiment are buffered.

In the context of the acid addition salt formed with methanesulphonic acid, a preferred buffer is a buffer formed from acetic acid and sodium acetate, for example at a solution pH of approximately 4.6. At this pH and in the acetate buffer, the methanesulphonic acid salt has a solubility of about 35 mg/ml.

The salts of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms therefore also form part of the invention.

The compound 4-(2,6-dichloro-benzoylamino)-1H-pyrazole-3-carboxylic acid piperidin-4-ylamide may also form N-oxides. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compound 4-(2,6-dichloro-benzoylamino)-1H-pyrazole-3-carboxylic acid piperidin-4-ylamide, from which the acid addition salts of the invention are derived, salts may exist in a number of different tautomeric forms and references in this application to the compound include all such forms.

More particularly, in the acid addition salts of the invention, the pyrazole ring of the 4-(2,6-dichloro-benzoylamino)-1H-pyrazole-3-carboxylic acid piperidin-4-ylamide can exist in the two tautomeric forms A and B below. For simplicity, the formulae in this application show only form A but the formulae are to be taken nevertheless as embracing both tautomeric forms.

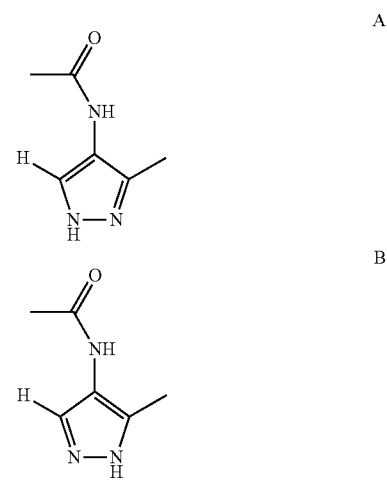

Moreover, in the context of the acid addition salts of the invention, references to 4-(2,6-dichloro-benzoylamino)-1H-pyrazole-3-carboxylic acid piperidin-4-ylamide and its salts also include variants with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by references to acid addition salts (e.g. the mesylate salt) of 4-(2,6-dichloro-benzoylamino)-1H-pyrazole-3-carboxylic acid piperidin-4-ylamide are any polymorphic forms, solvates (e.g. hydrates), complexes (e.g. inclusion complexes or clathrates with compounds such as cyclodextrins, or complexes with metals) thereof.

Crystal Structures of Acid Addition Salts of 4-(2,6-dichlorobenzoylamino)-1H-pyrazole-3-carboxylic acid piperidin-4-ylamide As described above, the acid addition salts of 4-(2,6-dichloro-benzoylamino)-1H-pyrazole-3-carboxylic acid piperidin-4-ylamide can be amorphous or substantially crystalline. In one particular embodiment, the salts are substantially crystalline, the term "substantially crystalline" having the meaning defined above. In particular the mesylate and acetate salts of 4-(2,6-dichlorobenzoyl-amino)-1H-pyrazole-3-carboxylic acid piperidin-4-ylamide are substantially crystalline.

The crystals described herein and their crystal structures form further aspects of the invention.

The crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to conventional methods, such as those described herein and in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal.

The crystal structure of the methanesulphonic acid salt of 4-(2,6-dichloro-benzoylamino)-1H-pyrazole-3-carboxylic acid piperidin-4-ylamide has been determined by X-ray crystallography—see Example 2 below.

Table 2 gives coordinate data for crystals of the 4-(2,6-dichlorobenzoylamino)-1H-pyrazole-3-carboxylic acid piperidin-4-ylamide mesylate salt in Crystallographic Information File (CIF) Format (see Hall, Allen and Brown, *Acta Cryst.* (1991). A47, 655-685; http://www.iucr.ac.uk/iucr-top/cif/home.html). Alternative file formats such as a PDB file format (e.g. format consistent with that of the EBI Macromolecular Structure Database (Hinxton, UK)) may be used or preferred by others of skill in the art. However it will be apparent that the use of a different file format to present or manipulate the coordinates of the Tables is within the scope of the present invention. The crystal structure of the mesylate salt is illustrated in FIGS. 1 and 2.

From the X-ray crystallography studies, it has been found that the mesylate salt has a crystal structure that belongs belong to an orthorhombic space group such as Pbca (#61) and has crystal lattice parameters at 93 K a=8.90(10), b=12.44(10), c=38.49(4) Å, α=β=γ=90°.

Accordingly, in another embodiment, the invention provides a methanesulphonic acid salt of 4-(2,6-dichlorobenzoylamino)-1H-pyrazole-3-carboxylic acid piperidin-4-ylamide which is crystalline and:
(a) has a crystal structure as set out in FIGS. 1 and 2; and/or
(b) has a crystal structure as defined by the coordinates in Example 2 herein; and/or
(c) has crystal lattice parameters at 93 K a=8.90(10), b=12.44(10), c=38.49(4) Å, α=β=γ=90°; and/or
(d) has a crystal structure that belongs belong to an orthorhombic space group such as Pbca (#61).

Alternatively, the crystalline structure of a compound can be analysed by the solid state technique of X-ray Powder Diffraction (XRPD). XRPD can be carried out according to conventional methods such as those described herein (see Example 6) and in Introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle (2θ) and interplanar spacing (d) parameters of an X-ray diffraction spectrum. These are related by Bragg's equation, nλ=2d Sin θ, (where n=1; λ=wavelength of the cathode used; d=interplanar spacing; and θ=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean ones which coincide in the range of 2θ+0.2°. The peaks mean main peaks and include peaks not larger than medium at diffraction angles other than those stated above.

Both the acetic acid and methanesulphonic acid salts of 4-(2,6-dichlorobenzoylamino)-1H-pyrazole-3-carboxylic acid piperidin-4-ylamide have been characterised by XRPD.

4-(2,6-Dichlorobenzoylamino)-1H-pyrazole-3-carboxylic acid piperidin-4-ylamide methanesulphonic acid salt has an X-ray powder diffraction pattern essentially as shown in FIG. 3

4-(2,6-Dichlorobenzoylamino)-1H-pyrazole-3-carboxylic acid piperidin-4-ylamide acetic acid salt has an X-ray powder diffraction pattern essentially as shown in FIG. 4.

In each case, the powder X-ray diffraction patterns are expressed in terms of the diffraction angle (2θ), inter planar spacing (d) and relative intensities.

Accordingly, in another embodiment, the invention provides a substantially crystalline methanesulphonic acid salt of 4-(2,6-dichlorobenzoylamino)-1H-pyrazole-3-carboxylic acid piperidin-4-ylamide having an X-ray powder diffraction pattern characterised by the presence of major peaks at the diffraction angles (2θ) and interplanar spacings (d) set forth in Table A.

TABLE A

| 2Θ/° | d/Å |
|---|---|
| 16.60 | 5.34 |
| 18.30 | 4.85 |
| 18.45 | 4.81 |
| 19.45 | 4.56 |
| 22.90 | 3.88 |

The X-ray powder diffraction pattern is preferably further characterised by the presence of additional peaks at the diffraction angles (2θ) and interplanar spacings (d) set forth in Table B.

TABLE B

| 2Θ/° | d/Å |
|---|---|
| 12.80 | 6.91 |
| 21.40 | 4.15 |
| 22.00 | 4.04 |
| 23.50 | 3.78 |
| 25.00 | 3.56 |

The X-ray powder diffraction pattern may also be characterised by the presence of peaks at the diffraction angles (2θ) and interplanar spacings (d), and preferably the intensities shown in Table C.

TABLE C

| 2Θ/° | d/Å | I |
|---|---|---|
| 4.55 | 19.41 | 12 |
| 10.80 | 8.19 | 9 |
| 12.25 | 7.22 | 15 |
| 12.80 | 6.91 | 56 |
| 13.40 | 6.60 | 12 |
| 13.55 | 6.53 | 26 |
| 14.00 | 6.32 | 7 |
| 14.75 | 6.00 | 8 |
| 15.50 | 5.71 | 25 |
| 16.60 | 5.34 | 100 |
| 17.30 | 5.12 | 15 |
| 17.75 | 4.99 | 16 |
| 18.30 | 4.85 | 90 |
| 18.45 | 4.81 | 65 |
| 19.45 | 4.56 | 65 |
| 20.80 | 4.27 | 18 |
| 21.40 | 4.15 | 40 |
| 22.00 | 4.04 | 42 |
| 22.90 | 3.88 | 71 |
| 23.50 | 3.78 | 45 |
| 23.90 | 3.72 | 27 |
| 24.40 | 3.65 | 32 |
| 25.00 | 3.56 | 61 |
| 26.00 | 3.43 | 18 |
| 26.50 | 3.36 | 20 |
| 27.00 | 3.30 | 30 |
| 28.00 | 3.18 | 14 |
| 28.40 | 3.14 | 14 |
| 28.70 | 3.11 | 17 |

The invention further provides a substantially crystalline methanesulphonic acid salt of 4-(2,6-dichlorobenzoyl-amino)-1H-pyrazole-3-carboxylic acid piperidin-4-ylamide which exhibits peaks at the same diffraction angles as those of the X-ray powder diffraction pattern shown in FIG. 3. Preferably the peaks have the same relative intensity as the peaks in FIG. 3.

In a preferred embodiment, the invention provides a substantially crystalline methanesulphonic acid salt of 4-(2,6-dichlorobenzoylamino)-1H-pyrazole-3-carboxylic acid piperidin-4-ylamide having an X-ray powder diffraction pattern substantially as shown in FIG. 3

The invention also provides a substantially crystalline acetic acid salt of 4-(2,6-dichlorobenzoylamino)-1H-pyrazole-3-carboxylic acid piperidin-4-ylamide which exhibits peaks at the same diffraction angles as those of the X-ray powder diffraction pattern shown in FIG. 4. Preferably the peaks have the same relative intensity as the peaks in FIG. 4.

In a preferred embodiment, the invention provides a substantially crystalline acetic acid salt of 4-(2,6-dichlorobenzoylamino)-1H-pyrazole-3-carboxylic acid piperidin-4-ylamide having an X-ray powder diffraction pattern substantially as shown in FIG. 4.

The crystalline acid addition salts of the invention can also be characterised by differential scanning calorimetry (DSC).

The mesylate salt has been analysed by DSC and exhibits a peak at 379.8° C. due to the decomposition of the compound.

Accordingly, in another aspect, the invention provides a mesylate salt of 4-(2,6-dichlorobenzoylamino)-1H-pyrazole-3-carboxylic acid piperidin-4-ylamide which is anhydrous and exhibits an endothermic peak at 379-380° C. e.g. 379.8° C. when subjected to DSC.

The acetate salt has been analysed by DSC and exhibits a peak at 231.50° C. due to the loss of acetic acid and a further peak at 292.88° C. due to the decomposition of the compound. The absence of peaks at lower temperatures indicates that the acetate salt is anhydrous.

Accordingly, in another aspect, the invention provides an acetic acid salt of 4-(2,6-dichlorobenzoylamino)-1H-pyrazole-3-carboxylic acid piperidin-4-ylamide which is anhydrous and exhibits endothermic peaks at 231-232° C. (e.g. 231.50° C.) and 292-293° C. (e.g. 292.88° C.) when subjected to DSC.

Where the acid addition salt of 4-(2,6-dichlorobenzoylamino)-1H-pyrazole-3-carboxylic acid piperidin-4-ylamide is substantially crystalline, one single crystalline form may predominate, although other crystalline forms may be present in minor and preferably negligible amounts.

In a preferred embodiment, the invention provides a substantially crystalline acid addition salt (e.g. a mesylate or acetate salt as defined herein) of 4-(2,6-dichlorobenzoylamino)-1H-pyrazole-3-carboxylic acid piperidin-4-ylamide containing a single crystalline form of the acid addition salt and no more than 5% by weight of any other crystalline forms of the acid addition salt.

Preferably, the single crystalline form is accompanied by less than 4%, or less than 3%, or less than 2% of other crystalline forms, and in particular contains less than or equal to about 1% by weight of other crystalline forms. More preferably, the single crystalline form is accompanied by less than 0.9%, or less than 0.8%, or less than 0.7%, or less than 0.6%, or less than 0.5%, or less than 0.4%, or less than 0.3%, or less than 0.2%, or less than 0.1%, or less than 0.05%, or less than 0.01%, by weight of other crystalline forms, for example 0% by weight of other crystalline forms.

The substantially crystalline acid addition salts preferably are substantially free of residual organic solvent used, e.g. to recrystallise or otherwise purify the salt, or other solvent such as water.

In one embodiment, therefore, the crystals of the acid addition salts (e.g. the methane-sulphonate or acetate salts) of 4-(2,6-dichlorobenzoylamino)-1H-pyrazole-3-carboxylic acid piperidin-4-ylamide are crystals which contain less than 10% by weight of residual solvent (e.g. water or an organic solvent), for example less than 5% residual solvent, e.g. less than 4% or less than 3%, or less than 2%, or less than 1%, or less than 0.5% solvent.

In one embodiment, the crystalline acid addition salts (e.g. the methane-sulphonate or acetate salts) are anhydrous, the term "anhydrous" having the meaning defined above.

The methanesulphonate salt can exist in a stable anhydrous crystalline form which, although absorbing some surface water in conditions of high relative humidity, does not undergo changes in crystal structure under such conditions.

The behaviour of the acid addition salts of the invention in conditions of high humidity can be analysed by standard gravimetric vapour sorption (GVS) methods, for example as described in Example 7.

The acid addition salts of the invention can be further characterised by infra-red spectroscopy, e.g. FTIR.

The infra-red spectrum of the methanesulphonate salt (KBr disc method) contains characteristic peaks at 3233, 3002, 2829, 1679, 1632, 1560, 1430, 1198, 1037, 909 and 784 cm$^{-1}$.

Accordingly, in a further embodiment, the invention provides a (preferably substantially crystalline) methanesulphonic acid salt of 4-(2,6-dichlorobenzoyl-amino)-1H-pyrazole-3-carboxylic acid piperidin-4-ylamide that exhibits an infra-red spectrum, when analysed using the KBr disc method , that contains characteristic peaks at 3233, 3002, 2829, 1679, 1632, 1560, 1430, 1198, 1037, 909 and 784 cm$^{-1}$.

As will be evident from the foregoing paragraphs, the acid addition salts of the invention can be characterised by a number of different physicochemical parameters. Accordingly, in a preferred embodiment, the invention provides a methanesulphonic acid salt of 4-(2,6-dichlorobenzoylamino)-1H-pyrazole-3-carboxylic acid piperidin-4-ylamide mesylate salt which is crystalline and is characterised by any one or more (in any combination) or all of the following parameters, namely that the salt:

(a) has a crystal structure as set out in FIGS. 1 and 2; and/or (b) has a crystal structure as defined by the coordinates in Example 2 herein; and/or (c) has crystal lattice parameters at 93 K a=8.90(10), b=12.44 (10), c=38.49(4) Å, α=β=γ=90°; and/or (d) has a crystal structure that belongs belong to an orthorhombic space group such as Pbca (#61); and/or (e) has an X-ray powder diffraction pattern characterised by the presence of major peaks at the diffraction angles (2θ) and interplanar spacings (d) set forth in Table A, and optionally Table B; for example wherein the X-ray powder diffraction pattern is characterised by the presence of major peaks at the diffraction angles (2θ), interplanar spacings (d) and intensities set forth in Table C herein; and/or (f) exhibits peaks at the same diffraction angles as those of the X-ray powder diffraction pattern shown in FIG. 3 and optionally wherein the peaks have the same relative intensity as the peaks in FIG. 3; and/or (g) has an X-ray powder diffraction pattern substantially as shown in FIG. 3; and/or (h) is anhydrous and exhibits an endothermic peak at 379-380° C. e.g. 379.8° C. when subjected to DSC; and/or (i) exhibits an infra-red spectrum, when analysed using the KBr disc method, that contains characteristic peaks at 3233, 3002, 2829, 1679, 1632, 1560, 1430, 1198, 1037, 909 and 784 cm$^{-1}$.

Processes for Preparing 4-(2,6-dichloro-benzoylamino)-1H-pyrazole-3-carboxylic acid piperidin-4-ylamide In Example 237 of our earlier application PCT/GB2004/003179 (WO 2005/012256), it is disclosed that 4-(2,6-dichloro-benzoylamino)-1H-pyrazole-3-carboxylic acid piperidin-4-ylamide can be prepared by a sequence of steps including:

(i) reacting 4-(2,6-dichloro-benzoylamino)-1H-pyrazole-3-carboxylic acid with 4-amino-1-tert-butyloxycarbonyl-piperidine in the presence of 1-ethyl-3-(3'-dimethylamino-propyl)-carbodiimide (EDC) and 1-hydroxybenzotriazole (HOBt) in dimethyl formamide (DMF) to give the N-Boc protected form of 4-(2,6-dichloro-benzoylamino)-1H-pyrazole-3-carboxylic acid piperidin-4-ylamide; and (ii) removing the Boc protecting group by treatment with hydrochloric acid.

It has now been found that instead of using EDC and HOBt to promote formation of the amide bond, the acid chloride of 4-(2,6-dichloro-benzoylamino)-1H-pyrazole-3-carboxylic acid may be reacted with a 4-aminopiperidine in which the piperidine nitrogen is protected.

Accordingly, in another aspect, the invention provides a process for preparing 4-(2,6-dichloro-benzoylamino)-1H-pyrazole-3-carboxylic acid piperidin-4-ylamide or a salt thereof, which process comprises the reaction of a compound of the formula (XI):

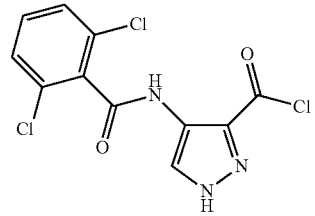

(XI)

with a compound of the formula (XII):

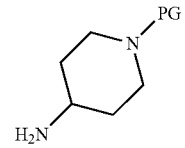

(XII)

where PG is an amine-protecting group, in an organic solvent in the presence of a non-interfering base such as triethylamine, to give a compound of the formula (XIII):

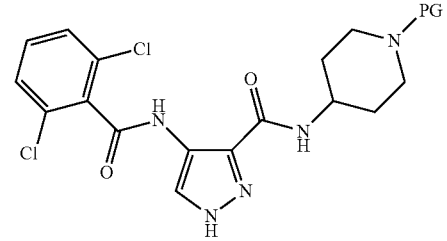

(XIII)

and thereafter removing the protecting group PG to give 4-(2,6-dichloro-benzoylamino)-1H-pyrazole-3-carboxylic acid piperidin-4-ylamide or salt thereof;
and optionally recrystallising the salt to give a crystalline form, e.g. a crystalline form as defined herein.

The amine-protecting group PG can be any protecting group known for use in protecting amine groups under the conditions used in the above process. Examples of protecting groups, and methods of protecting and deprotecting functional groups, can be found in *Protective Groups in Organic Synthesis* (T. Green and P. Wuts; 3rd Edition; John Wiley and Sons, 1999). Thus, for example, the piperidine ring nitrogen may be protected as an amide NCO—R) or a urethane (NCO—OR), for example, as: a methyl amide (NCO—CH$_3$); a benzyloxy amide (NCO—OCH$_2$C$_6$H$_5$, —NH-Cbz); as a tert-butoxy amide (—NCO—OC(CH$_3$)$_3$, N-Boc); a 2-biphenyl-2-propoxy amide (NCO—OC(CH$_3$)$_2$C$_6$H$_4$C$_6$H$_5$, N-Bpoc), as a 9-fluorenylmethoxy amide (N-Fmoc), as a 6-nitroveratryloxy amide (N-Nvoc), as a 2-trimethylsilyl-ethyloxy amide (N-Teoc), as a 2,2,2-trichloroethyloxy amide (N-Troc), as an allyloxy amide (N-Alloc), or as a 2-(phenyl-sulphonyl)ethyloxy amide (—N-Psec). Other protecting groups for amines include toluenesulphonyl (tosyl) and methanesulphonyl (mesyl) groups and benzyl groups such as a para-methoxybenzyl (PMB) group. Preferred amine protecting groups are a urethane (NCO—OR), for example, a benzyloxy amide (NCO—OCH$_2$C$_6$H$_5$, —NH-Cbz), or a tert-butoxy amide (—NCO—OC(CH$_3$)$_3$, N-Boc); an allyloxy amide (N-Alloc) or a para-methoxybenzyl (PMB) group. A particularly preferred protecting group PG is tert-butyloxycarbonyl which may be removed under acidic conditions.

Where the protecting group PG is one which may be removed under acidic conditions, the acid selected to remove the protecting group PG may be chosen so as to provide 4-(2,6-dichloro-benzoylamino)-1H-pyrazole-3-carboxylic acid piperidin-4-ylamide in a particular salt form. Thus, for example, when the protecting group is a Boc group, hydrochloric acid may be used to cleave the Boc protecting group and produce the hydrochloride salt of 4-(2,6-dichloro-benzoylamino)-1H-pyrazole-3-carboxylic acid piperidin-4-ylamide. Alternatively, and more preferably, methanesulphonic acid may be used to cleave the Boc group and produce the methanesulphonic acid salt of 4-(2,6-dichloro-benzoylamino)-1H-pyrazole-3-carboxylic acid piperidin-4-ylamide.

The invention also provides a method preparing an intermediate of the formula (XIII) by reacting the compound of formula (XI) with the compound of formula (XII) under the conditions defined herein.

The invention further provides a novel chemical intermediate per se of the formula (XI).

In another aspect, the invention provides a process for preparing 4-(2,6-dichloro-benzoylamino)-1H-pyrazole-3-carboxylic acid piperidin-4-ylamide or a salt thereof, which process comprises:
(i) treating a compound of the formula (XIV):

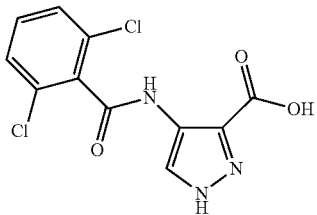

(XIV)

with thionyl chloride in a non-protic organic solvent, optionally with heating;
(ii) reacting the product of step (i) with a compound of the formula (XII) in the presence of a non-interfering base such as triethylamine optionally with heating, to give a compound of the formula (XIII); and
(iii) removing the protecting group PG from the compound of the formula (XIII) to give 4-(2,6-dichloro-benzoylamino)-1H-pyrazole-3-carboxylic acid piperidin-4-ylamide or a salt thereof; and optionally
(iv) recrystallising the salt to give a crystalline form, e.g. a crystalline form as defined herein.

In step (i), the reaction with thionyl chloride may be carried out with heating, for example to a temperature in the range 80 to 100° C. The solvent in which step (i) is carried out is a non-protic organic solvent, and it may be, for example, an aromatic hydrocarbon solvent such as toluene. Following completion of the reaction in step (i), as judged for example by the disappearance of starting material (XIV), the organic solvent may be removed, for example by evaporation under reduced pressure to give a residue which may be further dried, for example by azeotropic drying, to give a residue. The residue may then be reacted with the compound of the formula (XII) in step (ii).

In step (ii), a non-interfering base is used. The term "non-interfering base" in the present context means a base such as triethylamine which will not form an amide with the acid (XIII) or the acid chloride (XI).

Step (ii) is typically carried out with moderate heating, for example to a temperature of up to about 55° C., more typically up to 50° C., e.g. a temperature in the range 45° C. to 50° C.

In step (ii), the reaction may be carried out in a polar aprotic solvent such as tetrahydrofuran.

In step (iii), the protecting group is preferably one such as the Boc group that can be removed by treatment with acid, the acid being selected so as to give rise to a desired salt of 4-(2,6-dichloro-benzoylamino)-1H-pyrazole-3-carboxylic acid piperidin-4-ylamide, for example the methanesulphonic acid salt.

Following step (iii), the product may subjected to recrystallisation (e.g. using 2-propanol as the solvent) to increase the purity and to give a crystalline form.

When the protecting group PG is a tert-butyloxycarbonyl group, the overall yield from steps (i), (ii) and (iii) of the process, not including any recrystallisation steps, is in excess of 85%. Furthermore, the process is advantageous in that it makes use of relatively simple and inexpensive reagents and solvents, and gives product of greater than 99% purity using only simple recrystallisation and solvent washing techniques and without the need for chromatography.

Methods of recrystallisation of 4-(2,6-dichloro-benzoylamino)-1H-pyrazole-3-carboxylic acid piperidin-4-ylamide and its salts can be carried out by methods well known to the skilled person—see for example (P. Heinrich Stahl (Editor), Camille G. Wermuth (Editor), ISBN: 3-90639-026-8, Handbook of Pharmaceutical Salts: *Properties, Selection, and Use*, Chapter 8, Publisher Wiley-VCH). Products obtained from an organic reaction are seldom pure when isolated directly from the reaction mixture. If the compound (or a salt thereof) is solid, it may be purified and/or crystallized by recrystallization from a suitable solvent. A good recrystallization solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallizing solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

In some cases, traces of Boc-protected 4-(2,6-dichloro-benzoylamino)-1H-pyrazole-3-carboxylic acid piperidin-4- ylamide can remain even after recrystallisation and these may form a precipitate when the acid addition salt of the invention is dissolved in water, for example in a buffered solution. Aqueous solutions of the acid addition salts may therefore be subjected to filtration through a microfilter, e.g. a 0.5 µm filter, or a 0.4 µm filter, or a 0.3 µm filter, or more preferably a 0.2 µm filter, to remove any such precipitate.

As an alternative (or in addition) to filtration, an aqueous solution of the salt may be subjected to heating in the presence of an acid, typically the same acid (e.g. methanesulphonic acid in the case of the mesylate salt) from which the salt has been formed. The further acid treatment results in hydrolysis of residual Boc-protected 4-(2,6-dichloro-benzoylamino)-1H-pyrazole-3-carboxylic acid piperidin-4-ylamide and conversion to the desired salt.

Solvent-aqueous extractions or chromatography as set out in the examples below may also be used to remove or prevent the formation of precipitates of residual Boc-protected compound.

Biological Activity

The compound 4-(2,6-dichloro-benzoylamino)-1H-pyrazole-3-carboxylic acid piperidin-4-ylamide and its salts are inhibitors of cyclin dependent kinases. For example, they are inhibitors of cyclin dependent kinases selected from CDK1, CDK2, CDK3, CDK4, CDK5, CDK6 and CDK9, and in particular CDK1, CDK2, CDK3, CDK4, CDK5 and CDK9, and more particularly CDK1, CDK2, CDK4 and CDK9. They are also inhibitors of CDK8 and CDK11.

4-(2,6-Dichloro-benzoylamino)-1H-pyrazole-3-carboxylic acid piperidin-4-ylamide and its salts also have activity against glycogen synthase kinase-3 (GSK-3).

As a consequence of their activity in modulating or inhibiting CDK and glycogen synthase kinase, 4-(2,6-dichloro-benzoylamino)-1H-pyrazole-3-carboxylic acid piperidin-4-ylamide and its salts are expected to be useful in providing a means of arresting, or recovering control of, the cell cycle in abnormally dividing cells. It is therefore anticipated that they will prove useful in treating or preventing proliferative disorders such as cancers. It is also envisaged that they will be useful in treating conditions such as viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases for example.

One sub-group of disease states and conditions where it is envisaged that the salts of the invention will be useful consists of viral infections, autoimmune diseases and neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB−ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous Leukaemias, myelodysplastic syndrome, or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers may be cancers which are sensitive to inhibition of any one or more cyclin dependent kinases selected from CDK1, CDK2, CDK4, CDK6 and CDK9, for example, one or more CDK kinases selected from CDK1, CDK2, CDK4 and CDK9, e.g. CDK1 and/or CDK2.

Whether or not a particular cancer is one which is sensitive to inhibition by a cyclin dependent kinase may be determined by means of a cell growth assay as set out in the examples below or by a method as set out in the section headed "Methods of Diagnosis".

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anaemia and aplastic anaemia; degenerative diseases of the musculoskeletal system, for example, osteoporosis and arthritis, aspirin-sensitive rhinosinusitis, cystic fibrosis, multiple sclerosis, kidney diseases and cancer pain.

It has also been discovered that some cyclin-dependent kinase inhibitors can be used in combination with other anticancer agents. For example, the cyclin-dependent kinase inhibitor flavopiridol has been used with other anticancer agents in combination therapy.

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia.

Another particular cancer is mantle cell lymphoma.

Another particular cancer is diffuse large B cell lymphoma

A further sub-set of cancers includes breast cancer, ovarian cancer, colon cancer, prostate cancer, oesophageal cancer, squamous cancer and non-small cell lung carcinomas.

The activity of the acid addition salts of the invention as inhibitors of cyclin dependent kinases and glycogen synthase kinase-3 can be measured using the assays set forth in the examples below and the level of activity exhibited can be defined in terms of the $IC_{50}$ value.

Thus, for example, it is envisaged that the acid addition salts of the invention will be useful in alleviating or reducing the incidence of cancer.

The invention also provides inter alia:

An acid addition salt of 4-(2,6-dichloro-benzoylamino)-1H-pyrazole-3-carboxylic acid piperidin-4-ylamide, other than a hydrochloride salt, for use in the prophylaxis or treatment of a disease state or condition mediated by a cyclin dependent kinase or glycogen synthase kinase-3.

An acid addition salt of 4-(2,6-dichloro-benzoylamino)-1H-pyrazole-3-carboxylic acid piperidin-4-ylamide, other than a hydrochloride salt, for use in inhibiting tumour growth in a mammal.

An acid addition salt of 4-(2,6-dichloro-benzoylamino)-1H-pyrazole-3-carboxylic acid piperidin-4-ylamide, other than a hydrochloride salt, for use in inhibiting the growth of tumour cells (e.g. in a mammal).

A method for the prophylaxis or treatment of a disease state or condition mediated by a cyclin dependent kinase or glycogen synthase kinase-3, which method comprises administering to a subject in need thereof an acid addition salt of 4-(2,6-dichloro-benzoylamino)-1H-pyrazole-3-carboxylic acid piperidin-4-ylamide, other than a hydrochloride salt.

A method of inhibiting tumour growth in a mammal (e.g. a human), which method comprises administering to the mammal (e.g. a human) an effective tumour growth-inhibiting amount of an addition salt of 4-(2,6-dichloro-benzoylamino)-1H-pyrazole-3-carboxylic acid piperidin-4-ylamide, other than a hydrochloride salt.

A method of inhibiting the growth of tumour cells (e.g. tumour cells present in a mammal such as a human), which method comprises contacting the tumour cells with an effective tumour cell growth-inhibiting amount of an acid addition salt of 4-(2,6-dichloro-benzoylamino)-1H-pyrazole-3-carboxylic acid piperidin-4-ylamide, other than a hydrochloride salt.

A method for alleviating or reducing the incidence of a disease state or condition mediated by a cyclin dependent kinase or glycogen synthase kinase-3, which method comprises administering to a subject in need thereof an acid addition salt of 4-(2,6-dichloro-benzoylamino)-1H-pyrazole-3-carboxylic acid piperidin-4-ylamide, other than a hydrochloride salt.

A method for treating a disease or condition comprising or arising from abnormal cell growth in a mammal, which method comprises administering to the mammal an acid addition salt of 4-(2,6-dichloro-benzoylamino)-1H-pyrazole-3-carboxylic acid piperidin-4-ylamide, other than a hydrochloride salt, in an amount effective in inhibiting abnormal cell growth.

A method for alleviating or reducing the incidence of a disease or condition comprising or arising from abnormal cell growth in a mammal, which method comprises administering to the mammal an acid addition salt of 4-(2,6-dichloro-benzoylamino)-1H-pyrazole-3-carboxylic acid piperidin-4-ylamide, other than a hydrochloride salt, in an amount effective in inhibiting abnormal cell growth.

A method for treating a disease or condition comprising or arising from abnormal cell growth in a mammal, the method comprising administering to the mammal an acid addition salt of 4-(2,6-dichloro-benzoylamino)-1H-pyrazole-3-carboxylic acid piperidin-4-ylamide, other than a hydrochloride salt, in an amount effective to inhibit a cdk kinase (such as cdk1 or cdk2) or glycogen synthase kinase-3 activity.

A method for alleviating or reducing the incidence of a disease or condition comprising or arising from abnormal cell growth in a mammal, the method comprising administering to the mammal an acid addition salt of 4-(2,6-dichloro-benzoylamino)-1H-pyrazole-3-carboxylic acid piperidin-4-ylamide, other than a hydrochloride salt, in an amount effective to inhibit a cdk kinase (such as cdk1 or cdk2) or glycogen synthase kinase-3 activity.

A method of inhibiting a cyclin dependent kinase or glycogen synthase kinase-3, which method comprises contacting the kinase with an acid addition salt of 4-(2,6-dichloro-benzoylamino)-1H-pyrazole-3-carboxylic acid piperidin-4-ylamide, other than a hydrochloride salt.

A method of modulating a cellular process (for example cell division) by inhibiting the activity of a cyclin dependent kinase or glycogen synthase kinase-3 using an acid addition salt of 4-(2,6-dichloro-benzoylamino)-1H-pyrazole-3-carboxylic acid piperidin-4-ylamide, other than a hydrochloride salt.

An acid addition salt of 4-(2,6-dichloro-benzoylamino)-1H-pyrazole-3-carboxylic acid piperidin-4-ylamide, other than a hydrochloride salt, for use in the prophylaxis or treatment of a disease state as described herein.

The use of an acid addition salt of 4-(2,6-dichloro-benzoylamino)-1H-pyrazole-3-carboxylic acid piperidin-4-ylamide, other than a hydrochloride salt, for the manufacture of a medicament, wherein the medicament is for any one or more of the uses defined herein.

A pharmaceutical composition comprising an acid addition salt of 4-(2,6-dichloro-benzoylamino)-1H-pyrazole-3-carboxylic acid piperidin-4-ylamide, other than a hydrochloride salt, and a pharmaceutically acceptable carrier.

A pharmaceutical composition for administration in an aqueous solution form, the pharmaceutical composition comprising an acid addition salt of 4-(2,6-dichloro-benzoylamino)-1H-pyrazole-3-carboxylic acid piperidin-4-ylamide, other than a hydrochloride salt, the salt having a solubility in water of greater than 15 mg/ml, typically greater than 20 mg/ml, preferably greater than 25 mg/ml, and more preferably greater than 30 mg/ml.

An acid addition salt of 4-(2,6-dichloro-benzoylamino)-1H-pyrazole-3-carboxylic acid piperidin-4-ylamide, other than a hydrochloride salt, for use in medicine.

An acid addition salt of 4-(2,6-dichloro-benzoylamino)-1H-pyrazole-3-carboxylic acid piperidin-4-ylamide, other than a hydrochloride salt, for any of the uses and methods set forth above, and as described elsewhere herein.

A method for the diagnosis and treatment of a disease state or condition mediated by a cyclin dependent kinase, which method comprises (i) screening a patient to determine whether a disease or condition from which the patient is or may be suffering is one which would be susceptible to treatment with a compound having activity against cyclin dependent kinases; and (ii) where it is indicated that the disease or condition from which the patient is thus susceptible, thereafter administering to the patient an acid addition salt of 4-(2,6-dichloro-benzoylamino)-1H-pyrazole-3-carboxylic acid piperidin-4-ylamide, other than a hydrochloride salt.

The use of an acid addition salt of 4-(2,6-dichloro-benzoylamino)-1H-pyrazole-3-carboxylic acid piperidin-4-ylamide, other than a hydrochloride salt, for the manufacture of a medicament for the treatment or prophylaxis of a disease state or condition in a patient who has been screened and has been determined as suffering from, or being at risk of suffering from, a disease or condition which would be susceptible to treatment with a compound having activity against cyclin dependent kinase.

The acid addition salts in the above aspects of the invention may be, for example, any of the salts described herein and particularly the methanesulphonate and acetate salts and mixtures thereof, and most preferably the methanesulphonate salt.

Treatment of B-Cell Lymphoma, Chronic Lymphocytic Leukaemia and Diffuse Large B Cell Lymphoma The invention also provides new uses (namely the use in the treatment of B-cell lymphoma, chronic lymphocytic leukaemia and diffuse large B cell lymphoma) of the compounds disclosed in our earlier application PCT/GB2004/003179 (WO 2005/012256), the contents of which are incorporated herein by reference.

More particularly, the invention provides the use of a compound of the formula (I°):

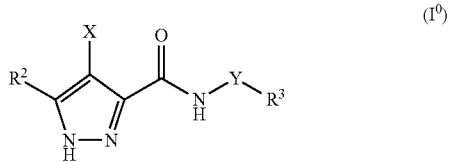

and sub-groups, embodiments and examples thereof as defined in PCT/GB2004/003179 (WO 2005/012256), and wherein $R^2$, $R^3$, X and Y are as defined in PCT/GB2004/003179 (WO 2005/012256), for the manufacture of a medicament for the treatment of B-cell lymphoma, chronic lymphocytic leukaemia or diffuse large B cell lymphoma.

Also provided are methods of treatment of B-cell lymphoma, diffuse large B cell lymphoma and chronic lymphocytic leukaemia by administering to a patient in need of such treatment a compound of the formula) (I°) as defined herein and in PCT/GB2004/003179 (WO 2005/012256).

Particular compounds of the formula (I°) are those defined in formula (Ib) on page 17, formula (II) on page 66, formula (IV) on page 72, formula (IVa) on page 74, formula (Va) on page 76, formula (Vb) on page 77, formula (VIa) on page 78 and formula VIb) on page 79 in WO 2005/012256, the compounds listed on page 79 and the compounds exemplified in the Examples section of WO 2005/012256.

A preferred compound of the formula) (I°) is 4-(2,6-dichloro-benzoylamino)-1H-pyrazole-3-carboxylic acid piperidin-4-ylamide and its salts (e.g. acid addition salts), solvates, tautomers or N-oxides.

In one embodiment, the salt may be a hydrochloride salt. The hydrochloride salt may be prepared as described in Example 150 or Example 237 of our earlier application PCT/GB2004/003179, the contents of which that are relevant to 4-(2,6-dichloro-benzoylamino)-1H-pyrazole-3-carboxylic acid piperidin-4-ylamide are incorporated herein by reference. Example 237 of PCT/GB2004/003179 (WO 2005/012256) is included in this application as Example 11.

Thus, according to this aspect of the invention, there is provided:

A compound of the formula) (I°) and sub-groups, embodiments and examples thereof as defined in PCT/GB2004/003179 (WO 2005/012256), and wherein and addition salts thereof (for example a hydrochloride salt) for use in the treatment of B-cell lymphoma.

A compound of the formula) (I°) and sub-groups, embodiments and examples thereof as defined in PCT/GB2004/003179 (WO 2005/012256), and wherein $R^2$, $R^3$, X and Y are as defined in PCT/GB2004/003179, and addition salts thereof (for example a hydrochloride salt) for use in the treatment of chronic lymphocytic leukaemia.

A compound of the formula) (I°) and sub-groups, embodiments and examples thereof as defined in PCT/GB2004/003179 (WO 2005/012256), and wherein $R^2$, $R^3$, X and Y are as defined in PCT/GB2004/003179, and addition salts thereof (for example a hydrochloride salt) for use in the treatment of diffuse large B cell lymphoma.

In a further aspect, the invention provides 4-(2,6-dichloro-benzoylamino)-1H-pyrazole-3-carboxylic acid piperidin-4-ylamide or a salt (e.g. an acid addition salt), solvate, tautomer or N-oxide thereof for use in the treatment of B-cell lymphoma.

The invention further provides 4-(2,6-dichloro-benzoylamino)-1H-pyrazole-3-carboxylic acid piperidin-4-ylamide or a salt (e.g. an acid addition salt), solvate, tautomer or N-oxide thereof for use in the treatment of chronic lymphocytic leukaemia.

The invention further provides 4-(2,6-dichloro-benzoylamino)-1H-pyrazole-3-carboxylic acid piperidin-4-ylamide or a salt (e.g. an acid addition salt), solvate, tautomer or N-oxide thereof for use in the treatment of diffuse large B cell lymphoma.

In the treatment of B-cell lymphoma, diffuse large B cell lymphoma and chronic lymphocytic leukaemia, the free base of 4-(2,6-dichloro-benzoylamino)-1H-pyrazole-3-carboxylic acid piperidin-4-ylamide may be employed or, more preferably, an acid addition salt may be used. The acid addition salt may be the hydrochloride salt disclosed in our earlier application PCT/GB2004/003179 (WO 2005/012256), or it may be one of the salts disclosed herein, for example the salts with methanesulphonic and acetic acids.

Also provided are methods of treatment of B-cell lymphoma, diffuse large B cell lymphoma and chronic lymphocytic leukaemia by administering to a patient in need of such treatment 4-(2,6-dichloro-benzoylamino)-1H-pyrazole-3-carboxylic acid piperidin-4-ylamide or an acid addition salt thereof.

Pharmaceutical Formulations

While it is possible for a compound (e.g. a compound of the formula) (I°) or 4-(2,6-dichloro-benzoylamino)-1H-pyrazole-3-carboxylic acid piperidin-4-ylamide or an acid addition salt thereof such as the mesylate salt) as defined herein to be administered alone, it is preferable to present it as a pharmaceutical composition (e.g. formulation) comprising the compound or salt thereof together with one or more pharmaceutically acceptable carriers, adjuvants, excipients, diluents, fillers, buffers, stabilisers, preservatives, lubricants, or other materials well known to those skilled in the art. The compositions may also include other therapeutic or prophylactic agents, for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Thus, the present invention further provides pharmaceutical compositions, as defined above, and methods of making a pharmaceutical composition comprising admixing a salt of 4-(2,6-dichloro-benzoylamino)-1H-pyrazole-3-carboxylic acid piperidin-4-ylamide (particularly the mesylate salt) as defined herein together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently far away from the formulation pH value. The acceptable range is pH 2-12 for intravenous and intramuscular administration, but for subcutaneous administration the acceptable range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to administration by IV bolus or IV infusion.

Alternatively increased water solubility can be achieved through molecular complexation with cyclodextrins Liposomes are closed spherical vesicles composed of outer lipid bilayer membranes and an inner aqueous core and with an overall diameter of <100 µm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at ~5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of Formulae (I°) or (I) or a salt thereof as defined herein. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediamietetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilised cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

Pharmaceutical compositions of the present invention for parenteral injection can also comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If a compound is not stable in aqueous media or has low solubility in aqueous media, it can be formulated as a concentrate in organic solvents. The concentrate can then be diluted to a lower concentration in an aqueous system, and can be sufficiently stable for the short period of time during dosing. Therefore in another aspect, there is provided a pharmaceutical composition comprising a non aqueous solution composed entirely of one or more organic solvents, which can be dosed as is or more commonly diluted with a suitable IV excipient (saline, dextrose; buffered or not buffered) before administration (Solubilizing excipients in oral and injectable formulations, Pharmaceutical Research, 21(2), 2004, p201-230). Examples of solvents and surfactants are propylene glycol, PEG300, PEG400, ethanol, dimethylacetamide (DMA), N-methyl-2-pyrrolidone (NMP, Pharmasolve), Glycerin, Cremophor EL, Cremophor RH 60 and polysorbate. Particular non aqueous solutions are composed of 70-80% propylene glycol, and 20-30% ethanol. One particular non aqueous solution is composed of 70% propylene glycol, and 30% ethanol. Another is 80% propylene glycol and 20% ethanol. Normally these solvents are used in combination and usually diluted at least 2-fold before IV bolus or IV infusion. The typical amounts for bolus IV formulations are ~50% for Glycerin, propylene glycol, PEG300, PEG400, and ~20% for ethanol. The typical amounts for IV infusion formulations are ~15% for Glycerin, 3% for DMA, and ~10% for propylene glycol, PEG300, PEG400 and ethanol.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing a compound of the formulae (I$^0$) or (I) or an acid addition salt thereof can be formulated in accordance with known techniques, see for example, Remington's Pharmaceutical Sciences, Mack Publishing Company, Easton, Pa., USA.

The compounds of the formula (I$^0$) and sub-formulae thereof, as defined in WO 2005/012256, can be formulated as described therein and as described in this application.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compound of the formulae ($I^0$) or (I) or acid addition salt thereof will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Methods of Treatment

It is envisaged that 4-(2,6-dichloro-benzoylamino)-1H-pyrazole-3-carboxylic acid piperidin-4-ylamide and its acid addition salts, in particular the mesylate, acetate and hydrochloride salts (and more particularly the mesylate and acetate salts and mixtures thereof), or the compounds of the formula) ($I^0$) as defined herein, will be useful in the prophylaxis or treatment of a range of disease states or conditions mediated by cyclin dependent kinases and glycogen synthase kinase-3. Examples of such disease states and conditions are set out above.

The compound and its salts are generally administered to a subject in need of such administration, for example a human or animal patient, preferably a human.

The compound and its salts will typically be administered in amounts that are therapeutically or prophylactically useful and which generally are non-toxic. However, in certain situations (for example in the case of life threatening diseases), the benefits of administering the compound or its salts may outweigh the disadvantages of any toxic effects or side effects, in which case it may be considered desirable to administer the compound or salt thereof in amounts that are associated with a degree of toxicity.

The compound or a salt thereof as defined herein may be administered over a prolonged term to maintain beneficial therapeutic effects or may be administered for a short period only. Alternatively they may be administered in a pulsatile or continuous manner.

A typical daily dose of the compound or a salt thereof as defined herein can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound or a salt thereof can be administered on a daily basis or on a repeat basis every 2, or 3, or 4, or 5, or 6, or 7, or 10 or 14, or 21, or 28 days for example.

An example of a dosage for a 60 kilogram person comprises administering a compound of the formula (I) as defined herein, for example the free base of compound 4-(2,6-dichloro-benzoylamino)-1H-pyrazole-3-carboxylic acid piperidin-4-ylamide at a starting dosage of 4.5-10.8 mg/60 kg/day (equivalent to 75-180 ug/kg/day) and subsequently by an efficacious dose of 44-97 mg/60 kg/day (equivalent to 0.7-1.6 mg/kg/day) or an efficacious dose of 72-274 mg/60 kg/day (equivalent to 1.2-4.6 mg/kg/day) although higher or lower doses may be administered where required. The mg/kg dose would scale pro-rata for any given body weight.

An example of a dosage for the mesylate salt is, at a starting dosage of 5.6-13.5 mg/60 kg/day (equivalent to 93-225 µg/kg/day/person) and subsequently by an efficacious dose of 55-122 mg/60 kg/day (equivalent to 0.9-2.0 mg/kg/day/person) or an efficacious dose of 90-345 mg/60 kg/day (equivalent to 1.5-5.8 mg/kg/day/person) although higher or lower doses may be administered where required. Ultimately, the quantity of compound administered and the type of composition used will be commensurate with the nature of the disease or physiological condition being treated and will be at the discretion of the physician.

In one particular dosing schedule, a patient will be given an infusion of the compound or a salt thereof for periods of one hour daily for up to ten days in particular up to five days for one week, and the treatment repeated at a desired interval such as two to four weeks, in particular every three weeks.

More particularly, a patient may be given an infusion of the compound or a salt thereof for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

In another dosage schedule, which can be used for example in the treatment of chronic lymphocytic leukaemia, a patient is given a 2 to 6 hour (more typically 3 to 5 hour) infusion, repeated at intervals of 6 to 8 days for 3, 4 or 5 weeks in 6. In a preferred embodiment of this schedule, a patient is given a four hour infusion, once weekly, for 4 weeks in 6.

Ultimately, however, the quantity of compound administered and the type of composition used will be commensurate with the nature of the disease or physiological condition being treated and will be at the discretion of the physician.

The compound or its salts can be administered as the sole therapeutic agent or they can be administered in combination therapy with one of more other compounds for treatment of a particular disease state, for example a neoplastic disease such as a cancer as hereinbefore defined. Examples of other therapeutic agents or therapies that may be administered or used together (whether concurrently or at different time intervals) with the compounds of the invention include but are not limited to topoisomerase inhibitors, alkylating agents, antimetabolites, DNA binders, microtubule inhibitors (tubulin targeting agents), monoclonal antibodies and signal transduction inhibitors, particular examples being cisplatin, cyclophosphamide, doxorubicin, irinotecan, fludarabine, 5FU, taxanes, mitomycin C and radiotherapy.

The compound or its salts and another therapeutic agent with which it is administered in a combination therapy may be given in individually varying dose schedules and via different routes. Thus, for example, the salt forms of 4-(2,6-dichlorobenzoylamino)-1H-pyrazole-3-carboxylic acid piperidin-4-ylamide (e.g. the mesylate and acetate salts and mixtures thereof) may be administered as solutions by the parenteral route whilst another therapeutic agent may be administered orally.

Where the compound of the formulae ($I^0$) or (I) or acid addition salt thereof are administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compound of the formulae ($I^0$) or (I) or acid addition salt thereof may also be administered in conjunction with non-chemotherapeutic treatments such as radiotherapy, photodynamic therapy, gene therapy; surgery and controlled diets.

For use in combination therapy with another chemotherapeutic agent, the compound of the formulae) ($I^0$) or (I) or acid addition salt thereof
and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimens and combination therapies to use.

Methods of Diagnosis

Prior to administration of a compound of the formulae ($I^0$) or (I) or an acid addition salts thereof, a patient may be screened to determine whether a disease or condition from which the patient is or may be suffering is one which would be susceptible to treatment with a compound having activity against cyclin dependent kinases.

For example, a biological sample taken from a patient may be analysed to determine whether a condition or disease, such as cancer, that the patient is or may be suffering from is one which is characterised by a genetic abnormality or abnormal protein expression which leads to over-activation of CDKs or to sensitisation of a pathway to normal CDK activity. Examples of such abnormalities that result in activation or sensitisation of the CDK2 signal include up-regulation of cyclin E, (Harwell R M, Mull B B, Porter D C, Keyomarsi K.; J Biol Chem. 2004 Mar. 26; 279(13):12695-705) or loss of p21 or p27, or presence of CDC4 variants (Rajagopalan H, Jallepalli P V, Rago C, Velculescu V E, Kinzler K W, Vogelstein B, Lengauer C.; Nature. 2004 Mar. 4; 428(6978):77-81). Tumours with mutants of CDC4 or up-regulation, in particular over-expression, of cyclin E or loss of p21 or p27 may be particularly sensitive to CDK inhibitors. The term up-regulation as used herein includes elevated expression or over-expression, including gene amplification (i.e. multiple gene copies) and increased expression by a transcriptional effect, and hyperactivity and activation, including activation by mutations.

Thus, the patient may be subjected to a diagnostic test to detect a marker characteristic of up-regulation of cyclin E, or loss of p21 or p27, or presence of CDC4 variants. The term diagnosis includes screening. By marker we include genetic markers including, for example, the measurement of DNA composition to identify mutations of CDC4. The term marker also includes markers which are characteristic of up regulation of cyclin E, including enzyme activity, enzyme levels, enzyme state (e.g. phosphorylated or not) and mRNA levels of the aforementioned proteins. Tumours with upregulation of cyclin E, or loss of p21 or p27 may be particularly sensitive to CDK inhibitors. Tumours may preferentially be screened for upregulation of cyclin E, or loss of p21 or p27 prior to treatment. Thus, the patient may be subjected to a diagnostic test to detect a marker characteristic of up-regulation of cyclin E, or loss of p21 or p27.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found, Rajagopalan et al (Nature. 2004 Mar. 4; 428(6978):77-81), that there were mutations present in CDC4 (also known as Fbw7 or Archipelago) in human colorectal cancers and endometrial cancers (Spruck et al, Cancer Res. 2002 Aug. 15; 62(16):4535-9). Identification of individual carrying a mutation in CDC4 may mean that the patient would be particularly suitable for treatment with a CDK inhibitor. Tumours may preferentially be screened for presence of a CDC4 variant prior to treatment. The screening process will typically involve direct sequencing, oligonucleotide microarray analysis, or a mutant specific antibody.

Methods of identification and analysis of mutations and up-regulation of proteins are well known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin E, or loss of p21 or p27, or detection of CDC4 variants could be applicable in the present case.

Therefore, all of these techniques could also be used to identify tumours particularly suitable for treatment with the compounds of the invention.

Tumours with mutants of CDC4 or up-regulation, in particular over-expression, of cyclin E or loss of p21 or p27 may be particularly sensitive to CDK inhibitors. Tumours may preferentially be screened for up-regulation, in particular over-expression, of cyclin E (Harwell R M, Mull B B, Porter D C, Keyomarsi K.; J Biol Chem. 2004 Mar. 26; 279(13): 12695-705) or loss of p21 or p27 or for CDC4 variants prior to treatment (Rajagopalan H, Jallepalli P V, Rago C, Velculescu V E, Kinzler K W, Vogelstein B, Lengauer C.; Nature. 2004 Mar. 4; 428(6978):77-81).

Patients with mantle cell lymphoma (MCL) could be selected for treatment with a compound of the invention using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11;14)(q13;q32) translocation. Over-expression of cyclin D1 mRNA, found in mantle cell lymphoma (MCL), is a critical diagnostic marker. Yatabe et al (Blood. 2000 Apr. 1; 95(7):2253-61) proposed that cyclin D1-positivity should be included as one of the standard criteria for MCL, and that innovative therapies for this incurable disease should be explored on the basis of the new criteria. Jones et al (J Mol Diagn. 2004 May; 6(2):84-9) developed a real-time, quantitative, reverse transcription PCR assay for cyclin D1 (CCND1) expression to aid in the diagnosis of mantle cell lymphoma (MCL). Howe et al (Clin Chem. 2004 January; 50(1):80-7) used real-time quantitative RT-PCR to evaluate cyclin D1 mRNA expression and found that quantitative RT-PCR for cyclin D1 mRNA normalized to CD19 mRNA can be used in the diagnosis of MCL in blood, marrow, and tissue. Alternatively, patients with breast cancer could be selected for treatment with a CDK inhibitor using diagnostic tests outline above. Tumour cells commonly overexpress cyclin E and it has been shown that cyclin E is overexpressed in breast cancer (Harwell et al, Cancer Res, 2000, 60, 481-489). Therefore breast cancer may in particular be treated with a CDK inhibitor as provided herein.

Antifungal Use

In a further aspect, the invention provides the use of an acid addition salt of 4-(2,6-dichloro-benzoylamino)-1H-pyrazole-3-carboxylic acid piperidin-4-ylamide, other than a hydrochloride salt, as an antifungal agent.

The acid addition salt of 4-(2,6-dichloro-benzoylamino)-1H-pyrazole-3-carboxylic acid piperidin-4-ylamide (other than a hydrochloride salt) may be used in animal medicine (for example in the treatment of mammals such as humans), or in the treatment of plants (e.g. in agriculture and horticulture), or as general antifungal agents, for example as preservatives and disinfectants.

In one embodiment, the invention provides an acid addition salt of 4-(2,6-dichloro-benzoylamino)-1H-pyrazole-3-carboxylic acid piperidin-4-ylamide, other than a hydrochloride salt, for use in the prophylaxis or treatment of a fungal infection in a mammal such as a human.

Also provided is the use of an acid addition salt of 4-(2,6-dichloro-benzoylamino)-1H-pyrazole-3-carboxylic acid piperidin-4-ylamide, other than a hydrochloride salt, for the manufacture of a medicament for use in the prophylaxis or treatment of a fungal infection in a mammal such as a human.

For example, the acid addition salts of the invention may be administered to human patients suffering from, or at risk of infection by, topical fungal infections caused by among other organisms, species of *Candida, Trichophyton, Microsporum* or *Epidermophyton*, or in mucosal infections caused by *Candida albicans* (e.g. thrush and vaginal candidiasis). The acid addition salts of the invention can also be administered for the treatment or prophylaxis of systemic fungal infections caused by, for example, *Candida albicans, Cryptococcus neoformans, Aspergillus flavus, Aspergillus fumigatus, Coccidiodies, Paracoccidioides, Histoplasma* or *Blastomyces*.

In another aspect, the invention provides an antifungal composition for agricultural (including horticultural) use, comprising an acid addition salt of 4-(2,6-dichloro-benzoylamino)-1H-pyrazole-3-carboxylic acid piperidin-4-ylamide, other than a hydrochloride salt, together with an agriculturally acceptable diluent or carrier.

The invention further provides a method of treating an animal (including a mammal such as a human), plant or seed having a fungal infection, which comprises treating said animal, plant or seed, or the locus of said plant or seed, with an effective amount of an acid addition salt of 4-(2,6-dichloro-benzoylamino)-1H-pyrazole-3-carboxylic acid piperidin-4-ylamide, other than a hydrochloride salt.

The invention also provides a method of treating a fungal infection in a plant or seed which comprises treating the plant or seed with an antifungally effective amount of a fungicidal composition containing an acid addition salt of 4-(2,6-dichloro-benzoylamino)-1H-pyrazole-3-carboxylic acid piperidin-4-ylamide, other than a hydrochloride salt.

Differential screening assays may be used to determine the specificity of the acid addition salts of the invention for non-human CDK enzymes. Salts which act specifically on the CDK enzymes of eukaryotic pathogens can be used as anti-fungal or anti-parasitic agents. Inhibitors of the *Candida* CDK kinase, CKSI, can be used in the treatment of candidiasis. Antifungal agents can be used against infections of the type hereinbefore defined, or opportunistic infections that commonly occur in debilitated and immunosuppressed patients such as patients with Leukaemias and lymphomas, people who are receiving immunosuppressive therapy, and patients with predisposing conditions such as diabetes mellitus or AIDS, as well as for non-immunosuppressed patients.

Assays described in the art can be used to screen for suitability in inhibiting at least one fungus implicated in mycosis such as candidiasis, aspergillosis, mucormycosis, blastomycosis, geotrichosis, cryptococcosis, chromoblastomycosis, coccidiodomycosis, conidiosporosis, histoplasmosis, maduromycosis, rhinosporidosis, nocardiosis, para-actinomycosis, penicilliosis, monoliasis, or sporotrichosis. The differential screening assays can be used to identify anti-fungal activity which may have therapeutic value in the treatment of aspergillosis by making use of the CDK genes cloned from yeast such as *Aspergillus fumigatus, Aspergillus flavus, Aspergillus niger, Aspergillus nidulans*, or *Aspergillus terreus*, or where the mycotic infection is mucon-nycosis, the CDK assay can be derived from yeast such as *Rhizopus arrhizus, Rhizopus oryzae, Absidia corymbifera, Absidia ramosa*, or *Mucor pusillus*. Sources of other CDK enzymes include the pathogen *Pneumocystis carinii*.

By way of example, in vitro evaluation of the antifungal activity of the acid addition salts of the invention can be performed by determining the minimum inhibitory concentration (M.I.C.) which is the concentration of the test compounds, in a suitable medium, at which growth of the particular microorganism fails to occur. In practice, a series of agar plates, each having the test compound incorporated at a particular concentration is inoculated with a standard culture of, for example, *Candida albicans* and each plate is then incubated for an appropriate period at 37° C. The plates are then examined for the presence or absence of growth of the fungus and the appropriate M.I.C. value is noted. Alternatively, a turbidity assay in liquid cultures can be performed and a protocol outlining an example of this assay can be found in the examples below.

The in vivo evaluation of the acid addition salts can be carried out at a series of dose levels by intraperitoneal or intravenous injection or by oral administration, to mice which have been inoculated with a fungus, e.g., a strain of *Candida albicans* or *Aspergillus flavus*. The activity of the salts can be assessed by monitoring the growth of the fungal infection in groups of treated and untreated mice (by histology or by retrieving fungi from the infection). The activity may be measured in terms of the dose level at which the compound provides 50% protection against the lethal effect of the infection ($PD_{50}$).

For human antifungal use, an acid addition salt of 4-(2,6-dichloro-benzoylamino)-1H-pyrazole-3-carboxylic acid piperidin-4-ylamide, other than a hydrochloride salt, can be administered alone or in admixture with a pharmaceutical carrier selected in accordance with the intended route of administration and standard pharmaceutical practice. Thus, for example, the salt may be administered orally, parenterally, intravenously, intramuscularly or subcutaneously by means of the formulations described above in the section headed "Pharmaceutical Formulations".

For oral and parenteral administration to human patients, the daily dosage level of the salt can be from 0.01 to 10 mg/kg (in divided doses), depending on inter alia the potency of the salts when administered by either the oral or parenteral route. Tablets or capsules of the salts may contain, for example, from 5 mg to 0.5 g of active compound for administration singly or two or more at a time as appropriate. The physician in any event will determine the actual dosage (effective amount) which will be most suitable for an individual patient and it will vary with the age, weight and response of the particular patient.

Alternatively, the salts can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

In addition to the therapeutic uses described above, antifungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms. In similar fashion, side by side comparison of inhibition of a mammalian CDK and an insect CDK, such as the *Drosophilia* CDK5 gene (Hellmich et al. (1994) FEBS Lett 356:317-21), will permit selection amongst the compounds herein of inhibitors which discriminate between the human/mammalian and insect enzymes. Accordingly, the present invention expressly contemplates the use and formulation of the salts of the invention in insecticides, such as for use in management of insects like the fruit fly.

In yet another embodiment, certain of the subject salts can be selected on the basis of inhibitory specificity for plant CDK's relative to the mammalian enzyme. For example, a plant CDK can be disposed in a differential screen with one or more of the human enzymes to select those compounds of greatest selectivity for inhibiting the plant enzyme. Thus, the present invention specifically contemplates formulations of the subject salts for agricultural applications, such as in the form of a defoliant or the like.

For agricultural and horticultural purposes the salts of the invention may be used in the form of a composition formulated as appropriate to the particular use and intended purpose. Thus the salts may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they can be manufactured in accordance with conventional procedures. The compositions may also incorporate other active ingredients, for example, compounds having herbicidal or insecticidal activity or a further fungicide. The salts and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack. By way of example, the compositions may contain from 0.01 to 1 wt. % of the active ingredient. For field use, likely application rates of the active ingredient may be from 50 to 5000 g/hectare.

The invention also contemplates the use of an acid addition salt of 4-(2,6-dichloro-benzoylamino)-1H-pyrazole-3-carboxylic acid piperidin-4-ylamide, other than a hydrochloride salt, in the control of wood decaying fungi and in the treatment of soil where plants grow, paddy fields for seedlings, or water for perfusion. Also contemplated by the invention is the use of an acid addition salt of 4-(2,6-dichloro-benzoylamino)-1H-pyrazole-3-carboxylic acid piperidin-4-ylamide, other than a hydrochloride salt, to protect stored grain and other non-plant loci from fungal infestation.

BRIEF DESCRIPTION OF THE DRAWINGS

FIG. 1 is a depiction of the three dimensional structure of 4-(2,6-dichlorobenzoylamino)-1H-pyrazole-3-carboxylic acid piperidin-4-ylamide methanesulphonate as determined by a single crystal X-ray diffraction study.

FIG. 2 is graphical representation of the structure generated by an X-ray diffraction study of 4-(2,6-dichlorobenzoylamino)-1H-pyrazole-3-carboxylic acid piperidin-4-ylamide methanesulphonate.

FIG. 3 is an X-ray powder diffractogram of 4-(2,6-dichlorobenzoylamino)-1H-pyrazole-3-carboxylic acid piperidin-4-ylamide methanesulphonic acid salt.

FIG. 4 is an X-ray powder diffractogram of 4-(2,6-dichlorobenzoylamino)-1H-pyrazole-3-carboxylic acid piperidin-4-ylamide acetic acid salt.

FIG. 5 is a DSC scan of the acetate salt of 4-(2,6-dichloro-benzoylamino)-1H-pyrazole-3-carboxylic acid piperidin-4-ylamide.

EXAMPLES

The invention will now be illustrated, but not limited, by reference to the specific embodiments described in the following examples.

Example 1

Synthesis of the methanesulphonic acid salt of 4-(2,6-dichloro-benzoylamino)-1H-pyrazole-3-carboxylic acid piperidin-4-ylamide and crystals thereof The methane sulphonic acid salt of 4-(2,6-dichloro-benzoylamino)-1H-pyrazole-3-carboxylic acid piperidin-4-ylamide may be prepared by the synthetic route shown in the Scheme below.

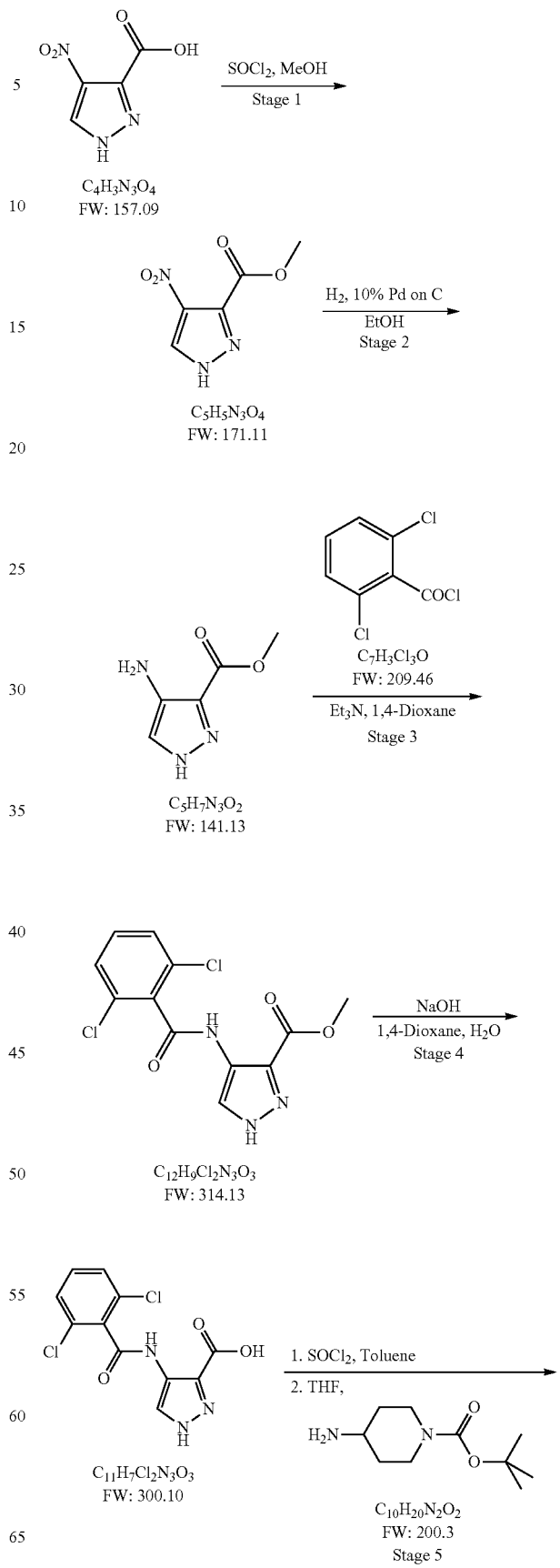

-continued

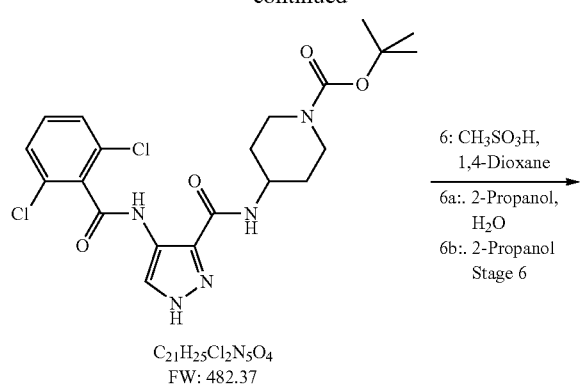

C₂₁H₂₅Cl₂N₅O₄
FW: 482.37

6: CH₃SO₃H, 1,4-Dioxane
6a:. 2-Propanol, H₂O
6b:. 2-Propanol
Stage 6

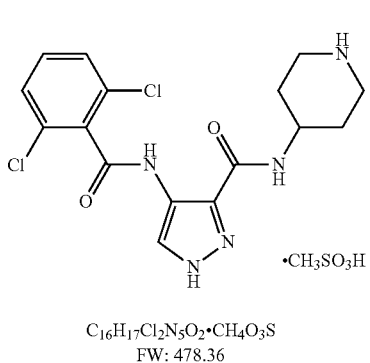

C₁₆H₁₇Cl₂N₅O₂·CH₄O₃S
FW: 478.36

·CH₃SO₃H

Stage 1: Preparation of 4-nitro-1H-pyrazole-3-carboxylic acid methyl ester

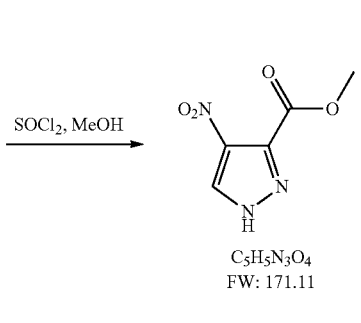

C₄H₃N₃O₄
FW: 157.09

SOCl₂, MeOH

C₅H₅N₃O₄
FW: 171.11

A 20 L reaction vessel equipped with a digital thermometer and stirrer was charged with 4-nitro-1H-pyrazole-3-carboxylic acid (1.117 Kg, 7.11 mol, 1 wt) and methanol (8.950 L, 8 vol). The reaction mixture was stirred under nitrogen, cooled to 0 to 5° C., thionyl chloride (0.581 L, 8.0 mol, 0.52 vol) added over 180 minutes and the resultant mixture allowed to warm to and stir at 18 to 22° C. overnight, after which time ¹H NMR analysis (d₆-DMSO) indicated reaction completion. The reaction mixture was concentrated under reduced pressure at 40 to 45° C., the residue treated with toluene and re-concentrated (3×2.250 L, 3×2 vol) under reduced pressure at 40 to 45° C. to give 4-nitro-1H-pyrazole-3-carboxylic acid methyl ester as an off-white solid (1.210 Kg, 99.5%).

Stage 2: Preparation of 4-amino-1H-pyrazole-3-carboxylic acid methyl ester

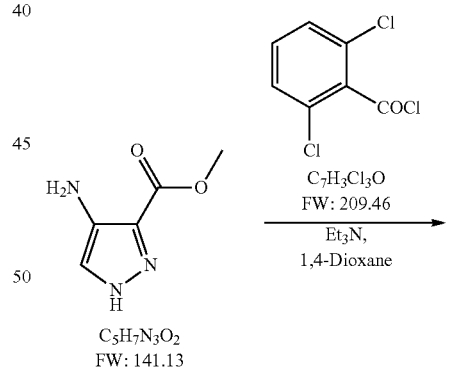

C₅H₅N₃O₄
FW: 171.11

H₂, 10% Pd on C
EtOH

C₅H₇N₃O₂
FW: 141.13

A 20 L reaction vessel equipped with a digital thermometer and stirrer was charged with palladium on carbon (10% wet paste, 0.170 Kg, 0.14 wt) under nitrogen. In a separate vessel a slurry of 4-nitro-1H-pyrazole-3-carboxylic acid methyl ester (1.210 Kg, 7.07 mol, 1 wt) in ethanol (12.10 L, 10 vol) was warmed to 30 to 35° C. to effect dissolution and the solution added to the catalyst under nitrogen. Following a nitrogen-hydrogen purge sequence an atmosphere of hydrogen was introduced and the reaction mixture maintained at 28 to 30° C. until reaction completion (5 to 10 hours) was noted by ¹H NMR analysis (d₆-DMSO). Following a purge cycle, the reaction mixture under nitrogen was filtered and the liquors concentrated under reduced pressure to give 4-amino-1H-pyrazole-3-carboxylic acid methyl ester (0.987 Kg, 98.9%).

Stage 3: Preparation of 4-(2,6-dichlorobenzoylamino)-1H-pyrazole-3-carboxylic acid methyl ester

C₅H₇N₃O₂
FW: 141.13

C₇H₃Cl₃O
FW: 209.46

Et₃N, 1,4-Dioxane

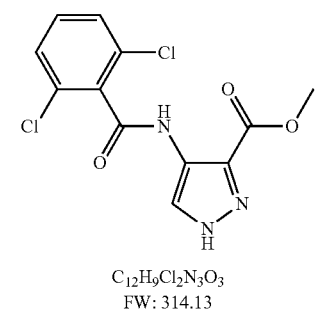

C₁₂H₉Cl₂N₃O₃
FW: 314.13

A solution of 4-amino-1H-pyrazole-3-carboxylic acid methyl ester (0.634 Kg, 4.49 mol, 1 wt) in 1,4-dioxane (8.90 L, 9 vol) under nitrogen was treated with triethylamine (0.761 L, 5.46 mol, 1.2 vol) followed by 2,6-dichlorobenzoyl chloride (0.710 L, 4.96 mol, 0.72 vol) such that the internal temperature was maintained in the range 20 to 25° C. Residual 2,6-dichlorobenzoyl chloride was washed in with a line rinse of 1,4-dioxane (0.990 L, 1 vol) and the reaction mixture stirred at 18 to 25° C. until complete (16 hours) by TLC analysis (eluent: ethyl acetate:heptanes 3:1; $R_{f\ amine}$ 0.25, $R_{f\ product}$ 0.65). The reaction mixture was filtered, the filter-cake washed with 1,4-dioxane (2×0.990 L, 2×1 vol) and the combined filtrates (red) progressed to Stage 4 without further isolation.

Stage 4: Preparation of 4-(2,6-dichlorobenzoylamino)-1H-pyrazole-3-carboxylic acid

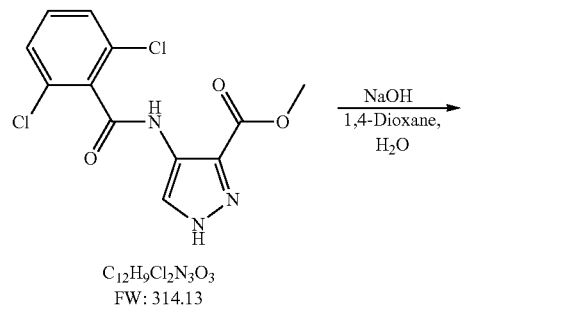

C$_{12}$H$_9$Cl$_2$N$_3$O$_3$
FW: 314.13

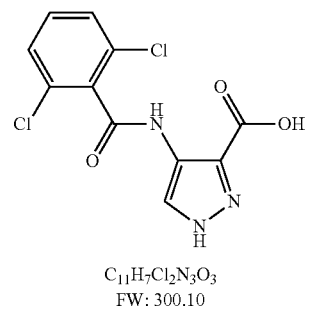

C$_{11}$H$_7$Cl$_2$N$_3$O$_3$
FW: 300.10

To a solution of sodium hydroxide (0.484 Kg, 12.1 mol) in water (6.05 L) was charged a solution of the Stage 3 ester in one portion: (1.099 Kg, 3.50 mol in 6.00 L). The reaction mixture was stirred to completion at 20 to 25° C. as determined by TLC analysis (eluent: ethyl acetate:heptanes 3:1; $R_{f\ ester}$ 0.65, $R_{f\ Stage\ 4}$ baseline). The reaction mixture was concentrated under reduced pressure at 45 to 50° C., the oily residue diluted with water (9.90 L) and acidified to pH 1 with concentrated hydrochloric acid such that the temperature was maintained below 30° C. The resulting precipitate was collected by filtration, washed with water (5.00 L), pulled dry on the filter and subsequently washed with heptanes (5.00 L). The filter-cake was charged to a 20 L rotary evaporator flask and drying completed azeotropically with toluene (2×4.50 L) to afford 4-(2,6-dichlorobenzoylamino)-1H-pyrazole-3-carboxylic acid as a yellow solid (1.044 Kg, approx. 99.5%).

Stage 5: Preparation of 4-{[4-(2,6-dichlorobenzoylamino)-1H-pyrazole-3-carbonyl]amino}piperidine-1-carboxylic acid tert-butyl ester

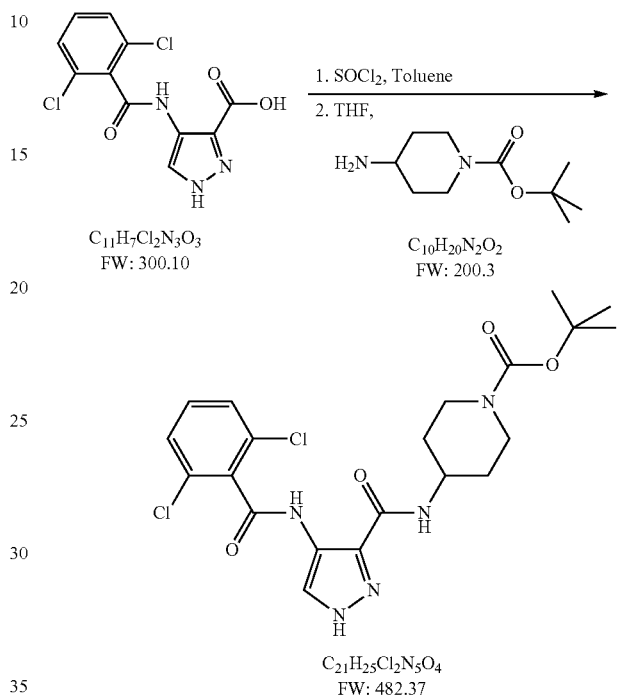

Stage 4 product (1.0 wt) and toluene (10.0 vol) were charged to a suitably sized flange flask equipped with a mechanical stirrer, dropping funnel and thermometer. The contents were stirred under nitrogen at 16 to 25° C. and thionyl chloride (0.3 vol) was added slowly. The contents were then heated to 80 to 100° C. and stirred at this temperature until the reaction was judged complete by $^1$H NMR. Further toluene (up to 10 vol) could be added at this stage if the contents were to become too thick to stir. Once complete, the mixture was cooled to between 40 and 50° C. and then concentrated under vacuum at 45 to 50° C. to dryness. The residue was then azeo-dried with toluene (3×2.0 vol).

The isolated solid was transferred to a suitably sized flask and tetrahydrofuran (5.0 vol) was charged. The contents were stirred under nitrogen at 16 to 25° C. and triethylamine (0.512 vol) was added. To a separate flask was charged 4-amino-piperidine-1-carboxylic acid tert-butyl ester (0.704 wt) and tetrahydrofuran (5.0 vol). The contents were agitated until complete dissolution was achieved and the solution was then charged to the reaction flask, maintaining the temperature between 16 and 30° C. The reaction mixture was then heated to between 45 and 50° C. and the contents stirred until judged complete by $^1$H NMR. The contents were then cooled to between 16 and 25° C. and water (5.0 vol) was charged. Mixed heptanes (0.5 vol) were added, the contents were stirred for up to 10 minutes and the layers were separated. The aqueous phase was then extracted with tetrahydrofuran:mixed heptanes [(9:1), 3×5.0 vol]. The organic phases were combined, washed with water (2.5 vol) and then concentrated under vacuum at 40 to 45° C. The residue was azeotroped with toluene (3×5.0 vol) and concentrated to dryness to yield the crude Stage 5 product.

The solid was then transferred to a suitably sized flask, methanol: toluene [(2.5:97.5), 5.0 vol] was added and the slurry was stirred under nitrogen for 3 to 18 hours. The contents were filtered, the filter-cake was washed with toluene (2×0.7 vol) and the solid was then dried under vacuum at 40 to 50° C. to yield 4-{[4-(2,6-dichlorobenzoylamino)-1H-pyrazole-3-carbonyl]amino}piperidine-1-carboxylic acid tert-butyl ester as an off-white solid.

Two batches of Stage 4 product (0.831 kg per batch) were processed in this way to give a total of 2.366 kg (88.6% yield) of 4-{[4-(2,6-dichlorobenzoylamino)-1H-pyrazole-3-carbonyl]amino}piperidine-1-carboxylic acid tert-butyl ester.

Stage 6: Preparation of 4-(2,6-dichlorobenzoylamino)-1H-pyrazole-3-carboxylic acid piperidin-4-ylamide methanesulphonate

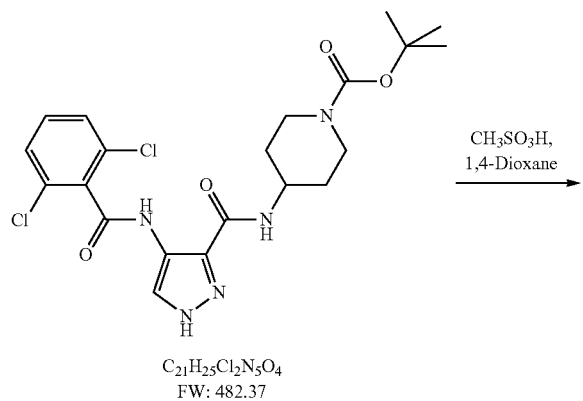

Stage 5 product (1.0 wt) and 1,4-dioxane (30.0 vol) were charged to a suitably sized flange flask equipped with a mechanical stirrer, dropping funnel and thermometer. The contents were stirred under nitrogen and heated to between 80 and 90° C. Methanesulphonic acid (0.54 vol) was added over 30 to 60 minutes and the contents were then heated to 95 to 105° C. and stirred in this temperature range until the reaction was judged complete by $^1$H NMR. Once complete, the contents were cooled to between 20 and 30° C. and the resultant precipitate collected by filtration. The filter-cake was washed with 2-propanol (2×2.0 vol) and pulled dry on the filter for 3 to 24 hours to give crude 4-(2,6-dichlorobenzoylamino)-1H-pyrazole-3-carboxylic acid piperidin-4-ylamide methanesulphonate as a free-flowing off-white solid (80.0 to 120.0% w/w, uncorrected for impurities or solutes).

Several batches of Stage 5 product were processed in this way and the details of the quantities of starting material and product for each batch are set out in Table 1 below.

TABLE 1

| | Yields from the deprotection step - Stage 6 | | |
|---|---|---|---|
| Batch | Input (g) of (4-{[4-(2,6-Dichlorobenzoylamino)-1H-pyrazole-3-carbonyl]-amino}-piperidine-1-carboxylic acid tert-butyl ester) | Output (g) of [4-(2,6-Dichlorobenzoyl-amino)-1H-pyrazole-3-carboxylic acid piperidine-4-ylamide methanesulphonate] | Chemical purity (HPLC % area) |
| 1 | 590.0 | 579.6 | 97.88 |
| | | 99.1% th, 98.2% w/w | |
| 2 | 521.0 | 532.7 | 98.09 |
| | | 103.1% th, 102.2% w/w | |
| 3 | 523.8 | 511.7 | 98.17 |
| | | 98.5% th, 97.7% w/w | |
| 4 | 518.4 | 596.3 | 98.24 |
| | | 116.0% th, 115.0% w/w | |
| 5 | 563.2 | 600.1 | 98.16 |
| | | 107.4% th, 106.6% w/w | |
| 6 | 563.1 | 565.2 | 98.49 |
| | | 101.2% th, 100.4% w/w | |
| 7 | 560.4 | 553.9 | 98.70 |
| | | 99.7% th, 98.8% w/w | |
| 8 | 569.7 | 560.6 | 98.41 |
| | | 99.2% th, 98.4% w/w | |

Stage 6a: Recrystallisation of 4-(2,6-dichlorobenzoylamino)-1H-pyrazole-3-carboxylic acid piperidin-4-ylamide methanesulphonate The product of Stage 6 was recrystallised to ensure that any residual levels of Boc-protected product of Stage 5 were no greater than 0.25%. Four batches of Stage 6 product were recrystallised using the following protocol.

Crude Stage 6 product and 2-propanol (10.0 vol) were charged to a suitably sized flask equipped with a mechanical stirrer, dropping funnel and thermometer. The contents were stirred under nitrogen and heated to between 75 and 85° C. Water (up to 2.5 vol) was then charged to the contents until a clear solution was obtained. The contents were then cooled to between 40 and 60° C. and concentrated under vacuum at 40 to 50° C. until the reaction volume was reduced by approximately 50%. 2-Propanol (3.0 vol) was charged to the flask and the contents were concentrated at 40 to 50° C. until approximately 3.0 vol of solvent was removed. This process was then repeated twice more with 2-propanol (2×3.0 vol) and the water content was checked. The resultant slurry was then cooled to between 0 and 5° C. and stirred at this temperature for 1 to 2 hours. The contents were filtered, the filter-cake was washed with 2-propanol (2×1.0 vol) and then pulled dry on the filter for up to 24 hours. The solid was transferred to drying trays and dried under vacuum at 45 to 50° C. to constant weight to give 4-(2,6-dichlorobenzoylamino)-1H-pyrazole-3-carboxylic acid piperidin-4-ylamide methanesulphonate as an off-white solid (60.0 to 100.0% w/w).

The recrystallisation yields for the four batches ranged between 85.6% and 90.4% and the purities of the recrystallised product ranged from 99.29% to 99.39%. A second recrystallisation increased the purity still further.

The 4-(2,6-dichlorobenzoylamino)-1H-pyrazole-3-carboxylic acid piperidin-4-ylamide methanesulphonate produced by this route had a melting point (by DSC) of 379.8° C.

The infra-red spectrum of the methanesulphonate salt (KBr disc method) included characteristic peaks at 3233, 3002, 2829, 1679, 1632, 1560, 1430, 1198, 1037, 909 and 784 cm$^{-1}$.

Without wishing to be bound by any theory, it is believed that the infra red peaks can be assigned to structural components of the salt as follow:

| Peak: | Due to: |
|---|---|
| 3233 cm$^{-1}$ | N—H |
| 3002 cm$^{-1}$ | aromatic C—H |
| 2829 cm$^{-1}$ | aliphatic C—H |
| 1679 cm$^{-1}$ | amide C=O |
| 1632, 1560 cm$^{-1}$ | amide |
| 1430 cm$^{-1}$ | aliphatic C—H |
| 1198 cm$^{-1}$ | SO$_2$—O |
| 1037 cm$^{-1}$ | C—Cl aromatic |
| 909, 784 cm$^{-1}$ | aromatic C—H |

Removal of Residual Boc-Protected Product of Stage 5

In some cases, when the methanesulphonate salt was dissolved in acetate buffer, a fine precipitate consisting of residual traces of the Boc-protected free base was observed. Several techniques may be used for removing or preventing the formation of the precipitate, as set out below.

(a) Filtration

A mixture of the methanesulphonate salt in 200 mM acetate buffer was drawn from a vial into a 20 mL single-use syringe using a sterile needle, and a clinical grade 0.2 μm filter (a Sartorius Minisart sterile single use filter unit) was then attached to the syringe. The plunger of the syringe was slowly depressed and the filtrate collected in a clean, clear glass vial. The content of the vial was a clear, colourless solution of the methanesulphonate salt free of particulate matter.

(b) Heating in Aqueous Acid

A mixture of the methanesulphonate salt and methanesulphonic acid (0.4 eq.) in water (10 vol) was heated at 100° C. for 4 hours, and then cooled to 60° C. Analysis by TLC indicates that the methanesulphonate salt was present as a single component. 2-Propanol (10 vol) was added and the mixture cooled to 40° C. The mixture was reduced in vacuo to approximately 10 volumes, then a further portion of 2-propanol added (10 vol) and the mixture again reduced to 10 volumes. This cycle was repeated a further three times. The mixture was cooled in an ice-bath and the solid formed collected by filtration, washed with 2-propanol (5 vol) and dried in vacuo to give the methanesulphonate salt as a white to off-white solid.

c) Organic-Aqueous Extractions

A mixture of the methanesulphonate salt and methanesulphonic acid (0.4 eq.) in water (10 vol) was heated at 100° C. for 3 hours, and then cooled to ambient temperature. To this mixture was added THF-heptane (9:1, 10 vol) and the resultant mixture stirred vigorously to give a solution. The layers were separated and the aqueous phase washed with THF-heptane (9:1, 2×10 vol) then ethyl acetate (2×10 vol). To the aqueous phase was added 2-propanol (10 vol) and the solution was reduced in vacuo to approximately 5 volumes, then a further portion of 2-propanol added (10 vol) and the mixture again reduced to 5 volumes. This cycle was repeated a further three times. The solid formed was collected by filtration, washed with 2-propanol (5 vol) and dried in vacuo to give the methanesulphonate salt as a white to off-white solid.

(d) Chromatography

The use of chromatographic techniques may provide a route for removing non-polar impurities from the methanesulphonate salt. It is envisaged that the use of reverse-phase methods will be particularly useful.

Example 2

Determination of the crystal structure of 4-(2,6-dichlorobenzoylamino)-1H-pyrazole-3-carboxylic acid piperidin-4-ylamide methanesulphonate by X-ray diffraction The compound 4-(2,6-dichlorobenzoylamino)-1H-pyrazole-3-carboxylic acid piperidin-4-ylamide methanesulphonate was prepared as described in Example 1. The crystal used for the diffraction experiment was a colourless plate with dimensions 0.05×0.08×0.14 mm$^3$ obtained by precipitation from a water solution by 2-propanol. Crystallographic data were collected at 93 K using CuKα radiation (λ=1.5418 Å) from a Rigaku rotating anode RU3HR, Osmic blue confocal optics and a Rigaku Jupiter CCD detector. Images were collected in two ω scans at 2θ=15 and 90° with a detector to crystal distance of 67 mm. Data collection was controlled by CrystalClear software and images were processed and scaled by Dtrek. Due to a high absorption coefficient (μ=4.01 mm$^{-1}$) data had to be corrected using 4$^{th}$ order Fourier absorption correction. It was found that the crystals belong to an orthorhombic space group Pbca (#61) with crystal lattice parameters at 93 K a=8.90(10), b=12.44(10), c=38.49(4) Å, α=β=γ=90°. The numbers in brackets represents the deviation (s.u., standard uncertainty).

The crystals described above and the crystal structure form a further aspect of the invention.

The crystal structure was solved using direct methods implemented in SHELXS-97. Intensity data for a total of 2710 unique reflections in a resolution range from 20-0.9 Å (2.3<θ<58.87) were used in the refinement of 271 crystallographic parameters by SHELXL-97. Final statistical parameters were: wR2=0.2115 (all data), R1=0.0869 (data with I>2σ(I)) and goodness of fit S=1.264.

One molecule of protonated free base and one mesylate anion were found in the asymmetric unit. The elemental composition of the asymmetric unit was C$_{17}$H$_{21}$Cl$_2$N$_5$O$_5$S and the calculated density of the crystals is 1.49 Mg/m$^3$. Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modelled by anisotropical thermal factors (see FIG. 1).

The crystal structure contains one intramolecular (N15H . . . O7 2.690 Å) and five intermolecular hydrogen bonds (see packing figure FIG. 2). Three of them link the protonated piperidine nitrogen with two mesylate anions. The first mesylate anion is linked through a single H-bond N12H12A . . . O2M 2.771 Å, while the second is involved in a bifurcated H-bond with interactions N12H12B . . . O1M 2.864 Å and N12H12B . . . O2M 3.057 Å. The remaining mesylate oxygen O3M is involved in a hydrogen bond N8H8 . . . O3M 2.928 Å. Neighbouring protonated free base molecules are linked together by a H-bond N15H15 . . . O7 2.876 Å, as well as by relatively long contact N15H15 . . . N2 3.562 Å and stacking of phenyl and pyrazole rings. These interactions are propagated infinitely along the b axis. Crystal packing contains 2D layers (in the ab plane) of mesylate anions sandwiched by an extensive network of charged H-bonds with two layers of protonated free base cations. The compact 2D sandwich layers are joined together along the c axis by stacking of phenyl rings and involving chlorine . . . phenyl interaction with C12 . . . C18 3.341 Å.

A graphical representation of the structure generated by the X-ray diffraction study is provided in FIG. 2.

The coordinates for the atoms making up the structure of the 4-(2,6-dichlorobenzoylamino)-1H-pyrazole-3-carboxylic acid piperidin-4-ylamide methanesulphonate are as set out in Table 2.

TABLE 2 space group: Pbca
unit cell at 93K with a, b & c having 5% s.u.:
a = 8.9
b = 12.4
c = 38.5
alpha = beta = gamma = 90
Coordinates in cif format:
loop_
_atom_site_label
_atom_site_type_symbol
_atom_site_fract_x
_atom_site_fract_y
_atom_site_fract_z
_atom_site_U_iso_or_equiv
_atom_site_adp_type
_atom_site_occupancy
_atom_site_symmetry_multiplicity
_atom_site_calc_flag
_atom_site_refinement_flags
_atom_site_disorder_assembly
_atom_site_disorder_group
S1M S 0.13517(17) 0.18539(13) 0.03193(5) 0.0286(5) Uani 1 1 d . . .
O1M O 0.1193(5) 0.2208(3) −0.00409(14) 0.0326(13) Uani 1 1 d . . .
O2M O 0.1551(5) 0.0681(3) 0.03330(13) 0.0331(13) Uani 1 1 d . . .
O3M O 0.0151(5) 0.2217(4) 0.05453(14) 0.0368(13) Uani 1 1 d . . .
C4M C 0.3036(8) 0.2420(6) 0.0475(2) 0.0355(19) Uani 1 1 d . . .
H4M1 H 0.3855 0.2197 0.0329 0.053 Uiso 1 1 calc R . . .
H4M2 H 0.3212 0.2181 0.0708 0.053 Uiso 1 1 calc R . . .
H4M3 H 0.2959 0.3189 0.0471 0.053 Uiso 1 1 calc R . . .
Cl1 Cl 0.26158(17) 0.18137(12) 0.34133(5) 0.0325(5) Uani 1 1 d . . .
Cl2 Cl 0.75698(19) 0.16766(13) 0.26161(5) 0.0366(6) Uani 1 1 d . . .
N1 N 0.6277(6) −0.2419(4) 0.34903(16) 0.0276(14) Uani 1 1 d . . .
H1 H 0.5932 −0.3064 0.3484 0.033 Uiso 1 1 calc R . . .
N2 N 0.7505(5) −0.2150(4) 0.36663(16) 0.0286(15) Uani 1 1 d . . .
C3 C 0.7635(7) −0.1082(5) 0.36163(19) 0.0265(17) Uani 1 1 d . . .
C4 C 0.6453(7) −0.0708(5) 0.34039(18) 0.0211(16) Uani 1 1 d . . .
C5 C 0.5616(7) −0.1594(5) 0.3322(2) 0.0277(18) Uani 1 1 d . . .
H5 H 0.4770 −0.1623 0.3181 0.033 Uiso 1 1 calc R . . .
C6 C 0.8878(7) −0.0454(5) 0.3760(2) 0.0269(17) Uani 1 1 d . . .
O7 O 0.9037(5) 0.0506(3) 0.36722(14) 0.0368(13) Uani 1 1 d . . .
N8 N 0.9821(6) −0.0939(4) 0.39821(15) 0.0267(14) Uani 1 1 d . . .
H8 H 0.9626 −0.1584 0.4048 0.032 Uiso 1 1 calc R . . .
C9 C 1.1147(7) −0.0417(5) 0.41139(19) 0.0253(17) Uani 1 1 d . . .
H9 H 1.1272 0.0261 0.3987 0.030 Uiso 1 1 calc R . . .
C10 C 1.1019(8) −0.0148(5) 0.4502(2) 0.0330(18) Uani 1 1 d . . .
H10A H 1.0156 0.0315 0.4540 0.040 Uiso 1 1 calc R . . .
H10B H 1.0866 −0.0804 0.4633 0.040 Uiso 1 1 calc R . . .
C11 C 1.2429(7) 0.0412(5) 0.4630(2) 0.0349(19) Uani 1 1 d . . .
H11A H 1.2533 0.1102 0.4515 0.042 Uiso1 1 calc R . . .
H11B H 1.2355 0.0538 0.4878 0.042 Uiso 1 1 calc R . . .
N12 N 1.3784(6) −0.0279(4) 0.45532(16) 0.0258(14) Uani 1 1 d . . .
H12A H 1.4618 0.0069 0.4623 0.031 Uiso 1 1 calc R . . .
H12B H 1.3716 −0.0892 0.4676 0.031 Uiso 1 1 calc R . . .
C13 C 1.3929(7) −0.0546(5) 0.4181(2) 0.0314(18) Uani 1 1 d . . .
H13A H 1.4790 −0.1013 0.4147 0.038 Uiso 1 1 calc R . . .
H13B H 1.4098 0.0107 0.4049 0.038 Uiso 1 1 calc R . . .
C14 C 1.2538(7) −0.1097(6) 0.4049(2) 0.0356(19) Uani 1 1 d . . .
H14A H 1.2425 −0.1785 0.4165 0.043 Uiso 1 1 calc R . . .
H14B H 1.2639 −0.1231 0.3802 0.043 Uiso 1 1 calc R . . .
N15 N 0.6215(5) 0.0371(4) 0.33108(16) 0.0256(14) Uani 1 1 d . . .
H15 H 0.6768 0.0852 0.3408 0.031 Uiso 1 1 calc R . . .
C16 C 0.5183(7) 0.0697(5) 0.30805(18) 0.0213(15) Uani 1 1 d . . .
O17 O 0.4336(5) 0.0082(3) 0.29260(13) 0.0309(12) Uani 1 1 d . . .
C18 C 0.5120(6) 0.1890(5) 0.30170(17) 0.0195(15) Uani 1 1 d . . .
C19 C 0.3923(7) 0.2486(5) 0.31620(19) 0.0252(16) Uani 1 1 d . . .
C20 C 0.3785(7) 0.3569(5) 0.30904(19) 0.0267(17) Uani 1 1 d . . .
H20 H 0.2991 0.3957 0.3185 0.032 Uiso 1 1 calc R . . .

TABLE 2-continued

C21 C 0.4814(7) 0.4078(5) 0.28805(19) 0.0270(17) Uani 1 1 d . . .
H21 H 0.4708 0.4808 0.2834 0.032 Uiso 1 1 calc R . . .
C22 C 0.6005(7) 0.3518(5) 0.27375(19) 0.0294(18) Uani 1 1 d . . .
H22 H 0.6702 0.3865 0.2597 0.035 Uiso 1 1 calc R . . .
C23 C 0.6142(7) 0.2425(5) 0.2807(2) 0.0286(17) Uani 1 1 d . . .

Example 3

Determination of the solubility of 4-(2,6-dichlorobenzoylamino)-1H-pyrazole-3-carboxylic acid piperidin-4-ylamide methanesulphonate The solubility of the 4-(2,6-dichlorobenzoylamino)-1H-pyrazole-3-carboxylic acid piperidin-4-ylamide methanesulphonate of Example 1 in aqueous solution at pH values ranging from 1 to 11 was investigated as described below.

Solutions were prepared by titrating standard hydrochloric acid with dilute sodium hydroxide solution to a desired pH. The solutions prepared had a pH ranging from 1 to 11. These solutions were then used to assess the solubility of 4-(2,6-dichlorobenzoylamino)-1H-pyrazole-3-carboxylic acid piperidin-4-ylamide methanesulphonate.

In each experiment, 150 mg of the methanesulphonate salt was weighed into a 5 ml clear vial and 3-4 ml of a solution of a given pH was added. The solution mixture was then stirred for an average of 3 hours at (i) ambient temperature and (ii) 4° C. In each case, the solution was then filtered through a 0.22 µm PVDF filter, the pH of the clear solution obtained was recorded, and the solution was assayed for methanesulphonate salt content using a UV-Vis spectrophotometer and standard solutions of the salt.

The solubility data obtained are shown in Tables 3 and 4. The data indicated that the solubility is pH and temperature dependent. The best solubilities were obtained between pH 4 and 7. At pH>7 and pH<3 precipitation of the salt was observed on standing at ambient temperature, although higher solubility was obtained initially.

TABLE 3

Mesylate salt solubility data obtained at ambient temperature

| Sample ID | Initial pH | Final pH | Absorbance at 260 nm | [Mesylate salt] (mg/ml) |
| --- | --- | --- | --- | --- |
| 1 | 0.26 | 0.37 | 0.2688 | 15.71 |
| 2 | 1.00 | 1.06 | 0.6928 | 40.29 |
| 3 | 2.51 | 3.00 | 0.7731 | 44.94 |
| 4 | 4.99 | 6.73 | 0.7622 | 44.31 |
| 5 | 7.34 | 7.30 | 0.765 | 44.47 |
| 6 | 8.17 | 7.40 | 0.7649 | 44.47 |
| 7 | 7.69 | 7.90 | 0.7241 | 42.10 |
| 8 | 9.04 | 7.4 | 0.6089 | 35.43 |
| 9 | 10.97 | 7.6 | 0.5949 | 34.61 |
| ‡10 | 0.504 | 0.50 | 0.2373 | 13.88 |

‡After 6 days in the laboratory, precipitation was observed in Solution 1. Once filtered this solution was assayed for mesylate salt content and the pH recorded

TABLE 4

Mesylate salt solubility data obtained at 4° C.

| Sample ID | Initial pH | Final pH | Absorbance at 260 nm | [Mesylate salt] (mg/ml) |
| --- | --- | --- | --- | --- |
| 1 | 0.26 | 0.26 | 0.1724 | 9.85 |
| 2 | 1.00 | 1.00 | 0.7350 | 39.41 |
| 3 | 2.51 | 2.51 | 0.735 | 41.49 |
| 4 | 4.99 | 4.99 | 0.7508 | 42.39 |

TABLE 4-continued

Mesylate salt solubility data obtained at 4° C.

| Sample ID | Initial pH | Final pH | Absorbance at 260 nm | [Mesylate salt] (mg/ml) |
|---|---|---|---|---|
| 5 | 7.34 | 7.34 | 0.8124 | 45.87 |
| 6 | 8.17 | 8.17 | 0.7343 | 43.17 |
| 7 | 7.69 | 7.69 | 0.6700 | 37.87 |
| 8 | 9.04 | 7.40 | 0.5372 | 30.36 |
| 9 | 10.97 | 7.90 | 0.5469 | 30.90 |

Example 4

Determination of the solubility of 4-(2,6-dichlorobenzoylamino)-1H-pyrazole-3-carboxylic acid piperidin-4-ylamide methanesulphonate in buffered solutions An investigation into the solubility of the mesylate salt of Example 1 in various buffering systems was carried out at ambient temperature and at 4° C. In a first set of experiments, the buffers selected were 200 mM succinate pH 5.5, citrate pH 5.5, and Tris/maleate pH 5.5, 6.5 and 7.5. A second set of buffers utilised included a 200 mM acetate pH 4.6, glycine/methanesulphonic acid pH 4.6 and glycine pH 5.5.
Buffer Preparations
Maleic Acid, Tris, Sodium Hydroxide Buffer Solution
This buffer was prepared by dissolving 23.62 g maleic acid and 24.2 g tris(hydroxymethyl)aminomethane in 1 liter of water. Volumes (50 ml) of this solution were titrated with 0.2M sodium hydroxide solution to the target pH and made up to 200 ml with water. Solutions of 0.2 M buffer of pH 5.5, 6.5 and 7.5 were prepared.
Succinic Acid, Sodium Hydroxide Buffer Solution
This buffer was prepared by dissolving 23.62 g succinic acid in 1 liter of water. A volume (50 ml) of this solution was titrated with 0.2M sodium hydroxide solution to the target pH and made up to 200 ml with water. A 0.2 M buffer solution of pH 5.5 was prepared.
Citric Acid, Sodium Citrate Buffer Solution
This buffer was prepared by dissolving 42.02 g citric acid in 1 liter of water. A volume (50 ml) of this solution was titrated with 0.2 M tri-sodium citrate solution (58.82 g in 1 liter of water) to the target pH and made up to 200 ml with water. A 0.2 M buffer solution of pH 5.5 was prepared.
Sodium Acetate, Acetic Acid Buffer
This buffer was prepared by dissolving 4.44 g sodium acetate in 200 ml water. A volume (50 ml) of this solution was titrated with 0.20 M acetic acid solution (1.3 ml in 200 ml water) and made up to 200 ml with water. A 0.20 M acetate buffer solution of pH 4.6 was prepared.
Glycine Solution
This buffer was prepared by dissolving 3.01 g glycine in 200 ml water. A 0.20 M glycine solution of pH 4.9 was prepared.
Methanesulphonate Salt Solubility Study in Buffers
With each pH and buffer system, two experiments were performed, one at ambient temperature and one at 4° C. In each experiment, to 4.0 ml buffer solution was added a nominal 220 mg of the mesylate salt and the solution mixture was stirred. The stirring was stopped after 3 hours, the solution filtered through a PVDF 0.22 μm membrane filter, diluted in sample diluent and assayed for mesylate salt content by HPLC. Throughout the experiments, the mesylate salt content of each sample was calculated using single point calibration each time.

The results are shown in Tables 5 and 6.

TABLE 5

Mesylate salt solubility data in acetate buffer 200 mM at 4° C.

| Sample ID | Buffer used | Initial pH | Final pH | [mesylate salt] (mg/ml) |
|---|---|---|---|---|
| 1 | Acetate | 4.6 | 4.6 | 37.16 |

TABLE 6

Mesylate salt solubility data in acetate buffer 200 mM at ambient temperature.

| Sample ID | Buffer used | Initial pH | Final pH | [Mesylate salt] (mg/ml) |
|---|---|---|---|---|
| 1 | Acetate | 4.6 | 4.5 | 30.65 |

From the results, it was found that the solubility of the mesylate salt lay between 32 and 37 mg/ml in acetate buffer. Autoclaving at 121° C. for 15 minutes, followed by heating the solution further at 40° C., 55° C. or 75° C. for 10-12 days, were carried out on the acetate buffered salt solution. The solution pH and 4-(2,6-dichlorobenzoylamino)-1H-pyrazole-3-carboxylic acid piperidin-4-ylamide methanesulphonate were found to be stable under these test conditions. Freeze-thaw stability tests on the acetate buffered salt solution did not result in precipitation of 4-(2,6-dichlorobenzoylamino)-1H-pyrazole-3-carboxylic acid piperidin-4-ylamide or its salt, and the solution pH and 4-(2,6-dichlorobenzoylamino)-1H-pyrazole-3-carboxylic acid piperidin-4-ylamide methanesulphonate were found to be stable under these test conditions.

Example 5

Determination of the stability of 4-(2,6-dichlorobenzoylamino)-1H-pyrazole-3-carboxylic acid piperidin-4-ylamide methanesulphonate Samples of the methanesulphonate salt of Example 1 were stored in sealed bags inside a sealed container at a temperature of 40° C. and in an atmosphere of 75% relative humidity for a period of six months. At periods of 1 month, 3 months and 6 months, various tests were carried out to determine whether any changes to the purity or physical state of the salt had occurred. The tests were as follows:
(a) Visual examination of the colour and physical appearance of the salt.
(b) Fourier Transform Infra Red (FTIR) spectroscopy—comparison with reference standard spectrum.
(c) Determination of melting point by differential scanning calorimetry (DSC).
(d) Determination of water content by a coulometric method using the coulometric reagent AKX.
(e) Analysis of impurities by HPLC.

The results of the tests are set out in Table 7. As can be seen, the colour and appearance of the salt remained unchanged over six months (test (a)) and the infra-red spectrum (test (b)) showed no changes over this period. In test (c), there was no decrease in melting point thus indicating that degradation of the salt was not occurring, and this was supported by the HPLC analyses which showed that none of the impurities present in the sample at time zero had increased in concentration during the period of the test.

Thus, the stability tests demonstrated that the methanesulphonate salt has good stability over a prolonged period.

Example 6

X-Ray Powder Diffraction Studies on 4-(2,6-dichlorobenzoylamino)-1H-pyrazole-3-carboxylic acid piperidin-4-ylamide methanesulphonic acid salt X-Ray powder diffraction (XRPD) analysis of the mesylate salt as prepared in Example 1 was carried out on a Bruker D500 diffractometer equipped with a rotating stage and a variable temperature stage. The radiation source was a sealed copper tube (Cu Kα radiation: 1.5406 Å) and the voltage and current were set at 40 kV and 40 mA. The detector used was a scintillation counter. The XRPD analyses were performed using the Diffrac Plus XRD Commander software v2.3.1.

Samples were prepared by lightly pressing a ca. 10 mg sample of the salt into the sample holder and then smoothing lightly to obtain a flat surface.

Diffractograms were collected over the range 3° to 40°, 2-Theta, with a step size of 0.001° and a step time of 1 second.

A diffractogram of the mesylate salt is shown in FIG. 3

The hydrochloride salt was taken up in MeOH and passed through a Strata-NH2 column, eluting with MeOH. The product-containing fractions were reduced in vacuo to give 4-(2,6-dichlorobenzoylamino)-1H-pyrazole-3-carboxylic acid piperidin-4-ylamide free base. To a mixture of the free base in MeOH was added MsOH (70% in water) and the mixture was stirred at ambient for 14 hours, then reduced in vacuo, azeotroping with toluene (×3). The residue was purified by trituration with acetone and dried in the vacuum oven to give the mesylate salt.

Samples of the mesylate salt produced by the method described above were run on a Hiden IGASorp moisture sorption analyser running CFRSorp software. The sample sizes were typically 10 mg. Moisture adsorption-desorption isotherms were performed as set out in the following table:

| Adsorption | Desorption |
|---|---|
| 40 | 85 |
| 50 | 75 |
| 60 | 65 |

TABLE 7

Summary of analytical results for the methanesulphonate salt stability trial in 40° C./75% relative humidity

| Stability tests | Specification | t = 0 | t = 1 month | t = 3 months | t = 6 months |
|---|---|---|---|---|---|
| | Pull Date | | 15 Oct 04 | 16 Nov 04 | 14 Jan 05 | 15 Apr 05 |
| | Analysis period | | 15-25 Oct 04 | 16-18 Nov 04 | 14-19 Jan 05 | 14-19 Jan 05 |
| (a) Description | To be reported | | Off-white solid | Off-white solid | Off-white solid | Off-white solid |
| (b) Identity by FTIR | Conforms to reference standard spectrum AS76/R/001 (UATR, 4000-650 cm$^{-1}$) | | Conforms to reference standard spectrum AS76/R/001 (UATR, 4000-650 cm$^{-1}$) | Conforms to reference standard spectrum AS76/R/001 (UATR, 4000-650 cm$^{-1}$) | Conforms to reference standard spectrum AS76/R/001 (UATR, 4000-650 cm$^{-1}$) | Conforms to reference standard spectrum AS76/R/001 (UATR, 4000-650 cm$^{-1}$) |
| (c) Melting point by DSC | To be reported (40→450° C. at 10° C./min, high pressure pan) | | Melting endotherm 367.7° C. | Melting endotherm 368.3° C. | Melting endotherm 375.5° C. | Melting endotherm 369.1° C. |
| (d) Water content | (AKX reagent) | | <0.1% w/w | <0.1% w/w | <0.1% w/w | <0.1% w/w |
| (e) Impurities (by HPLC) Total impurities | To be reported | | 0.52% area | 0.49% area | 0.50% area | 0.50% area |
| RRT 0.812 | | | 0.07% area | 0.07% area | 0.06% area | 0.06% area |
| RRT 1.196 | | | 0.01% area | 0.02% area | nd | nd |
| RRT 1.226 | | | 0.02% area | nd | 0.02% area | 0.02% area |
| RRT 1.303 | | | 0.02% area | 0.06% area | nd | nd |
| RRT 1.318 | | | 0.03% area | nd | 0.04% area | 0.04% area |
| RRT 1.484 | | | 0.15% area | 0.17% area | 0.17% area | 0.17% area |
| RRT 1.526 | | | 0.03% area | nd | 0.04% area | 0.03% area |
| RRT 1.680 | | | 0.19% area | 0.17% area | 0.17% area | 0.17% area |
| RRT 1.682 | | | nd | nd | nd | 0.01% area |
| Chemical purity | To be reported | | 99.48% area | 99.51% area | 99.50% area | 99.50% area |

Key to table
nd = not detected

Example 7

Studies on the Effect of Varying Relative Humidity 4-(2,6-dichlorobenzoylamino)-1H-pyrazole-3-carboxylic acid piperidin-4-ylamide methanesulphonic acid salt (i) Gravimetric Vapour Sorption (GVS) studies were carried out to investigate the behaviour of the mesylate salt in conditions of varying humidity. The mesylate salt used in the studies was prepared from the hydrochloride salt (see Example 11) by the following method.

-continued

| Adsorption | Desorption |
|---|---|
| 70 | 45 |
| 80 | 35 |
| 90 | 25 |
| | 15 |
| | 5 |
| | 0 |
| | 10 |
| | 20 |
| | 30 |

A double cycle was run using a sample of 12.92 mg of the mesylate salt. The resulting GVS isotherm demonstrated that the salt picked up approximately 4% in weight of water over the range 0% relative humidity to 90% relative humidity. However, provided that the salt is not exposed to relative humidities of more than 80%, the water uptake is less than 2.6% w/w. Importantly, water which was taken up during the adsorption stage was lost during the desorption state indicating the uptake of water is a surface effect.

(ii) In a separate test, approximately 10 mg of the mesylate salt as prepared above was pressed flat onto a glass slide to achieve a high surface area and placed in a dessicator containing a saturated aqueous solution of sodium chloride. This in turn was placed in an incubator held at 40° C. to provide an atmosphere of approximately 75% relative humidity. The sample was removed on 8 and 18 days and the XRPD profiles of the sample at these times were compared to the XRPD profile of the salt prior to commencement of the test. No changes were observed in the XRPD profiles. HPLC analysis indicated that no degradation of the salt had occurred during the test.

Tests (i) and (ii) above illustrate that although the mesylate salt does take up some water when exposed to conditions of high humidity, the water taken up is lost as the relative humidity drops and there is no change in the crystal structure of the salt. The mesylate salt is therefore a stable anhydrous salt.

Example 8

Preparation of 4-(2,6-dichloro-benzoylamino)-1H-pyrazole-3-carboxylic acid piperidin-4-ylamide acetic acid salt

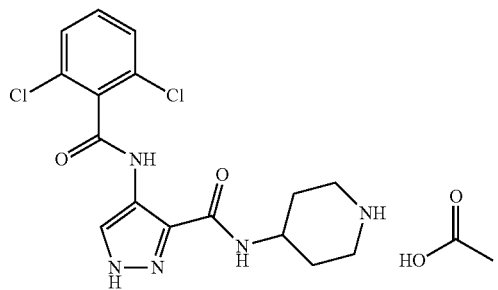

To a solution of 4-(2,6-dichloro-benzoylamino)-1H-pyrazole-3-carboxylic acid piperidin-4-ylamide hydrochloride salt (20.6 g, 50 mmol) in water (500 ml) stirring at ambient temperature was added sodium bicarbonate (4.5 g, 53.5 mmol). The mixture was stirred for 1 hour and the solid formed collected by filtration and dried in vacuo azeotroping with toluene (×3) to give the corresponding free base of 4-(2,6-dichloro-benzoylamino)-1H-pyrazole-3-carboxylic acid piperidin-4-ylamide.

$^1$H NMR (400 MHz, DMSO-$d_6$) δ 10.20 (s, 1H), 8.30 (s, 1H), 8.25 (d, 1H), 7.60-7.50 (m, 3H), 3.70 (m, 1H), 3.00 (d, 2H), 2.50 (m, 2H), 1.70 (d, 2H), 1.50 (m, 2H).

To a stirred suspension of 4-(2,6-dichloro-benzoylamino)-1H-pyrazole-3-carboxylic acid piperidin-4-ylamide (10.0 g, 26.2 mmol) in methanol (150 ml) was added glacial acetic acid (15 ml, 262 mmol) at ambient temperature. After 1 h, a clear solution was obtained which was reduced in vacuo azeotroping with toluene (×2). The residue was then triturated with acetonitrile (2×100 ml) and the solid dried in vacuo to give 4-(2,6-dichloro-benzoylamino)-1H-pyrazole-3-carboxylic acid piperidin-4-ylamide acetic acid salt (10.3 g) as a white solid.

$^1$H NMR (400 MHz, DMSO-$d_6$) δ 10.20 (s, 1H), 8.40 (d, 1H), 8.35 (s, 1H), 7.60-7.50 (m, 3H), 3.85 (m, 1H), 3.00 (d, 2H), 2.60 (t, 2H), 1.85 (s, 3H), 1.70 (d, 2H), 1.55 (m, 2H)

Example 9

Differential Scanning Calorimetry Studies on 4-(2,6-dichlorobenzoylamino)-1H-pyrazole-3-carboxylic acid piperidin-4-ylamide acetic acid salt The acetate salt of Example 8 was subjected to DSC studies using a TA instrument Q1000 equipped with a 50 position autosampler. Indium was used as an energy and temperature calibration standard.

Samples were heated at a rate of 10° C./minute between 10° C. and 230° C. A nitrogen purge at 30 ml/minute was maintained over the sample. Sample sizes of between 1 mg and 3 mg were used and all samples were crimped in a hermetically sealed pan. A DSC scan of the acetate salt is set out in FIG. 5. DSC trace shows an event at 231.5° C., which is attributed to the loss of acetic acid and subsequent conversion to the free base. On further heating the solid form decomposes/melts at 292.9° C.

Example 10

X-Ray Powder Diffraction Studies on 4-(2,6-dichlorobenzoylamino)-1H-pyrazole-3-carboxylic acid piperidin-4-ylamide acetic acid salt X-Ray powder diffraction (XRPD) analysis of the acetate salt of Example 8 was carried out on a Bruker D500 diffractometer according to the method described in Example 6.

A diffractogram of the acetate salt is shown in FIG. 4.

Example 11

Preparation of 4-(2,6-dichloro-benzoylamino)-1H-pyrazole-3-carboxylic acid piperidin-4-ylamide hydrochloride 11A. Synthesis of 4-nitro-1H-pyrazole-3-carboxylic acid methyl ester

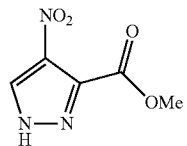

Thionyl chloride (2.90 ml, 39.8 mmol) is slowly added to a mixture of 4-nitro-3-pyrazolecarboxylic acid (5.68 g, 36.2 mmol) in methanol (100 ml) at ambient temperature and the mixture is stirred for 48 hours. The mixture is reduced in vacuo and dried through azeotrope with toluene to afford the 4-nitro-1H-pyrazole-3-carboxylic acid methyl ester.

11B. Synthesis of 4-amino-1H-pyrazole-3-carboxylic acid methyl ester

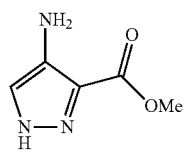

A mixture of 4-nitro-1H-pyrazole-3-carboxylic acid methyl ester (34.6 mmol) and 10% Pd/C (650 mg) in EtOH (150 ml) is stirred under an atmosphere of hydrogen for 20 hours. The mixture is filtered through a plug of Celite, reduced in vacuo and dried through azeotrope with toluene to afford 4-amino-1H-pyrazole-3-carboxylic acid methyl ester 11C. 4-(2,6-dichloro-benzoylamino)-1H-pyrazole-3-carboxylic acid 2,6-Dichlorobenzoyl chloride (8.2 g; 39.05 mmol) was added cautiously to a solution of 4-amino-1H-pyrazole-3-carboxylic acid methyl ester (5 g; 35.5 mmol) and triethylamine (5.95 ml; 42.6 mmol) in dioxan (50 ml) then stirred at room temperature for 5 hours. The reaction mixture was filtered and the filtrate treated with methanol (50 ml) and 2M sodium hydroxide solution (100 ml), heated at 50° C. for 4 hours, and then evaporated. 100 ml of water was added to the residue then acidified with concentrated hydrochloric acid. The solid was collected by filtration, washed with water (100 ml) and sucked dry to give 10.05 g of 4-(2,6-dichloro-benzoylamino)-1H-pyrazole-3-carboxylic acid as a pale violet solid.

11D. 4-{[4-(2,6-dichloro-benzoylamino)-1H-pyrazole-3-carbonyl]-amino}-piperidine-1-carboxylic acid tert-butyl ester A mixture of 4-(2,6-dichloro-benzoylamino)-1H-pyrazole-3-carboxylic acid (6.5 g, 21.6 mmol), 4-amino-1-BOC-piperidine (4.76 g, 23.8 mmol), EDC (5.0 g, 25.9 mmol) and HOBt (3.5 g, 25.9 mmol) in DMF (75 ml) was stirred at room temperature for 20 hours. The reaction mixture was reduced in vacuo and the residue partitioned between ethyl acetate (100 ml) and saturated aqueous sodium bicarbonate solution (100 ml). The organic layer was washed with brine, dried (MgSO$_4$) and reduced in vacuo. The residue was taken up in 5% MeOH-DCM (~30 ml). The insoluble material was collected by filtration and, washed with DCM and dried in vacuo to give 4-{[4-(2,6-dichloro-benzoylamino)-1H-pyrazole-3-carbonyl]-amino}-piperidine-1-carboxylic acid tert-butyl ester (5.38 g) as a white solid. The filtrate was reduced in vacuo and the residue purified by column chromatography using gradient elution 1:2 EtOAc/hexane to EtOAc to give further 4-{[4-(2,6-dichloro-benzoylamino)-1H-pyrazole-3-carbonyl]-amino}-piperidine-1-carboxylic acid tert-butyl ester (2.54 g) as a white solid.

11E. 4-(2,6-dichloro-benzoylamino)-1H-pyrazole-3-carboxylic acid piperidin-4-ylamide A solution of 4-{[4-(2,6-dichloro-benzoylamino)-1H-pyrazole-3-carbonyl]-amino}-piperidine-1-carboxylic acid tert-butyl ester (7.9 g) in MeOH (50 mL) and EtOAc (50 ml) was treated with sat. HCl-EtOAc (40 mL) then stirred at r.t. overnight. The product did not crystallise due to the presence of methanol, and therefore the reaction mixture was evaporated and the residue triturated with EtOAc. The resulting off white solid was collected by filtration, washed with EtOAc and sucked dry on the sinter to give 6.3 g of 4-(2,6-dichloro-benzoylamino)-1H-pyrazole-3-carboxylic acid piperidin-4-ylamide as the hydrochloride salt. (LC/MS: R$_t$ 5.89, [M+H]$^+$ 382/384).

Biological Activity

Example 12

Measurement of Activated CDK2/CyclinA Kinase Inhibitory Activity Assay (IC$_{50}$)

CDK2 kinase inhibitory activity may be determined using the following protocol.

Activated CDK2/CyclinA (Brown et al, Nat. Cell Biol., 1, pp 438-443, 1999; Lowe, E. D., et al Biochemistry, 41, pp 15625-15634, 2002) is diluted to 125 pM in 2.5× strength assay buffer (50 mM MOPS pH 7.2, 62.5 mM β-glycerophosphate, 12.5 mM EDTA, 37.5 mM MgCl$_2$, 112.5 mM ATP, 2.5 mM DTT, 2.5 mM sodium orthovanadate, 0.25 mg/ml bovine serum albumin), and 10 µl mixed with 10 µl of histone substrate mix (60 µl bovine histone H1 (Upstate Biotechnology, 5 mg/ml), 940 µl H$_2$O, 35 µCi γ$^{33}$P-ATP) and added to 96 well plates along with 5 µl of various dilutions of the test compound in DMSO (up to 2.5%). The reaction is allowed to proceed for 2 to 4 hours before being stopped with an excess of ortho-phosphoric acid (5 µl at 2%). γ$^{33}$P-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 µl of 0.5% orthophosphoric acid. Once the filters have dried, 20 µl of Microscint 20 scintillant is added, and then counted on a Packard Topcount for 30 seconds.

The % inhibition of the CDK2 activity is calculated and plotted in order to determine the concentration of test compound required to inhibit 50% of the CDK2 activity (IC$_{50}$).

The compound 4-(2,6-dichlorobenzoylamino)-1H-pyrazole-3-carboxylic acid piperidin-4-ylamide has an IC$_{50}$ value of less than 0.1 µM in the above CDK2 assay.

Example 13

Measurement of Activated CDK1/CyclinB Kinase Inhibitory Activity Assay (IC$_{50}$)

CDK1/CyclinB assay is identical to the CDK2/CyclinA above except that CDK1/CyclinB (Upstate Discovery) is used and the enzyme is diluted to 6.25 nM.

The compound 4-(2,6-dichlorobenzoylamino)-1H-pyrazole-3-carboxylic acid piperidin-4-ylamide has an IC$_{50}$ value of less than 0.1 µM in the above CDK1 assay.

Example 14

GSK3-B Kinase Inhibitory Activity Assay

GSK3-β (Upstate Discovery) are diluted to 7.5 nM in 25 mM MOPS, pH 7.00, mg/ml BSA, 0.0025% Brij-35, 1.25% glycerol, 0.5 mM EDTA, 25 mM $MgCl_2$, 0.025% β-mercaptoethanol, 37.5 mM ATP and 10 μl mixed with 10 μl of substrate mix. The substrate mix for GSK3-β is 12.5 μM phospho-glycogen synthase peptide-2 (Upstate Discovery) in 1 ml of water with 35 μCi $\gamma^{33}$P-ATP. Enzyme and substrate are added to 96 well plates along with 5 μl of various dilutions of the test compound in DMSO (up to 2.5%). The reaction is allowed to proceed for 3 hours (GSK3-β) before being stopped with an excess of ortho-phosphoric acid (5 μl at 2%). The filtration procedure is as for Activated CDK2/CyclinA assay above.

The compound 4-(2,6-dichlorobenzoylamino)-1H-pyrazole-3-carboxylic acid piperidin-4-ylamide has an $IC_{50}$ value of less than 0.1 μM in the above GSK3-B assay.

Example 15

Anti-proliferative Activity

The anti-proliferative activities of a compound can be determined by measuring the ability of the compound to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. Cell lines can be obtained from the ECACC (European Collection of cell Cultures).

Using this assay, the methanesulphonic acid salt of 4-(2,6-dichlorobenzoylamino)-1H-pyrazole-3-carboxylic acid piperidin-4-ylamide has been found to have an $IC_{50}$ value of 0.11 in HCT-116 cells.

Pharmaceutical Formulations

Example 16

(i) Tablet Formulation

A tablet composition containing a compound of the formulae ($I^0$) or (I) or an acid addition salt thereof as defined herein is prepared by mixing 50 mg of the compound or its salt with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formulae ($I^0$) or (I) or an acid addition salt thereof as defined herein with 100 mg lactose and filling the resulting mixture into standard opaque hard gelatin capsules.

(iii) Injectable Formulation I

A parenteral composition for administration by injection can be prepared by dissolving a compound of the formulae ($I^0$) or (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formulae ($I^0$) or (I) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formulae ($I^0$) or (I) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formulae ($I^0$) or (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formulae ($I^0$) or (I) or an acid addition salt thereof as defined herein, with pharmaceutical grade corn oil to give a concentration of 5 mg/ml. The composition is sterilised and filled into a suitable container.

viii) Lyophilised Formulation

Aliquots of formulated compound of formulae ($I^0$) or (I) or an acid addition salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Concentrate for Use in i.v. Administration

An aqueous buffered solution is prepared by dissolving 4-(2,6-dichlorobenzoylamino)-1H-pyrazole-3-carboxylic acid piperidin-4-ylamide methanesulphonate at a concentration of 20 mg/ml in a 0.2M sodium acetate/acetic acid buffer at a pH of 4.6.

The buffered solution is filled, with filtration to remove particulate matter, into a container (such as class 1 glass vials) which is then sealed (e.g. by means of a Florotec stopper) and secured (e.g. with an aluminium crimp). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. For intravenous administration, the solution can be dosed as is, or can be injected into an infusion bag (con-

Example 17

Determination of Antifungal Activity

The antifungal activity of a salt of 4-(2,6-dichlorobenzoylamino)-1H-pyrazole-3-carboxylic acid piperidin-4-ylamide can be determined using the following protocol.

The salts are tested against a panel of fungi including *Candida parpsilosis*, *Candida tropicalis*, *Candida albicans*-ATCC 36082 and *Cryptococcus neoformans*. The test organisms are maintained on Sabourand Dextrose Agar slants at 4° C. Singlet suspensions of each organism are prepared by growing the yeast overnight at 27° C. on a rotating drum in yeast-nitrogen base broth (YNB) with amino acids (Difco, Detroit, Mich.), pH 7.0 with 0.05 M morpholine propanesulphonic acid (MOPS). The suspension is then centrifuged and washed twice with 0.85% NaCl before sonicating the washed cell suspension for 4 seconds (Branson Sonifier, model 350, Danbury, Conn.). The singlet blastospores are counted in a haemocytometer and adjusted to the desired concentration in 0.85% NaCl.

The activity of the test compounds is determined using a modification of a broth microdilution technique. Test compounds are diluted in DMSO to a 1.0 mg/ml ratio then diluted to 64 µg/ml in YNB broth, pH 7.0 with MOPS (Fluconazole is used as the control) to provide a working solution of each compound. Using a 96-well plate, wells 1 and 3 through 12 are prepared with YNB broth, ten fold dilutions of the compound solution are made in wells 2 to 11 (concentration ranges are 64 to 0.125 µg/ml). Well 1 serves as a sterility control and blank for the spectrophotometric assays. Well 12 serves as a growth control. The microtitre plates are inoculated with 10 µl in each of well 2 to 11 (final inoculum size is $10^4$ organisms/ml). Inoculated plates are incubated for 48 hours at 35° C. The IC50 values are determined spectrophotometrically by measuring the absorbance at 420 nm (Automatic Microplate Reader, DuPont Instruments, Wilmington, Del.) after agitation of the plates for 2 minutes with a vortex-mixer (Vorte-Genie 2 Mixer, Scientific Industries, Inc., Bolemia, N.Y.). The IC50 endpoint is defined as the lowest drug concentration exhibiting approximately 50% (or more) reduction of the growth compared with the control well. With the turbidity assay this is defined as the lowest drug concentration at which turbidity in the well is <50% of the control (IC50). Minimal Cytolytic Concentrations (MCC) are determined by sub-culturing all wells from the 96-well plate onto a Sabourand Dextrose Agar (SDA) plate, incubating for 1 to 2 days at 35° C. and then checking viability.

Example 18

Protocol for the Biological Evaluation of Control of in vivo Whole Plant Fungal Infection A salt of 4-(2,6-dichlorobenzoylamino)-1H-pyrazole-3-carboxylic acid piperidin-4-ylamide is dissolved in acetone, with subsequent serial dilutions in acetone to obtain a range of desired concentrations. Final treatment volumes are obtained by adding 9 volumes of 0.05% aqueous Tween-20™ or 0.01% Triton X100™, depending upon the pathogen.

The compositions are then used to test the activity of the compounds of the invention against tomato blight (*Phytophthora infestans*) using the following protocol. Tomatoes (cultivar Rutgers) are grown from seed in a soil-less peat-based potting mixture until the seedlings are 10-20 cm tall. The plants are then sprayed to run-off with the test compound at a rate of 100 ppm. After 24 hours the test plants are inoculated by spraying with an aqueous sporangia suspension of *Phytophthora infestans*, and kept in a dew chamber overnight. The plants are then transferred to the greenhouse until disease develops on the untreated control plants.

Similar protocols are also used to test the activity of the compounds of the invention in combatting Brown Rust of Wheat (Puccinia), Powdery Mildew of Wheat (*Ervsiphe vraminis*), Wheat (cultivar Monon), Leaf Blotch of Wheat (*Septoria tritici*), and Glume Blotch of Wheat (*Leptosphaeria nodorum*).

Example 19

General Protocol for the Determination of the Solubilities of the Free Base and Salts of 4-(2,6-dichlorobenzoylamino)-1H-pyrazole-3-carboxylic acid piperidin-4-ylamide The solubilities of various salts of 4-(2,6-dichlorobenzoylamino)-1H-pyrazole-3-carboxylic acid piperidin-4-ylamide can be determined by means of the following protocol.

Procedure

Into an 8 ml vial is added the free base (50 mg, 0.131 mmol) and water (0.5 ml). To the vial is added the appropriate acid (1 eq., 0.131 mmol) and the vial is shaken at ambient temperature for 14-16 hours. After this time the vials are visually inspected. If a homogenous solution is observed, then the experiment is terminated, and it may be concluded that the salt thus formed has a solubility greater than 100 mg/ml.

If solid remains, then a further 0.5 ml of water is added and the vial is shaken for 6 hours. If a homogenous solution is formed by this stage, it may be concluded that the salt has a solubility of greater than 50 mg/ml.

If solid remains at this juncture, then a further 1 ml of water is added and the vial is shaken at ambient temperature. If this results in a homogenous solution, then it may be concluded that the solubility is greater than 25 mg/ml. If solid still remained, it may be concluded that the solubility of the salt is less than 25 mg/ml. Salt forms of the invention exhibit one or more of the following advantages over the free base, in that they:

will be more soluble and hence will be better for i.v. administration (e.g. by infusion)
will have better stability (e.g. improved shelf life);
will have better thermal stability;
will be less basic and therefore better for i.v. administration;
will have advantages for production;
will have improved solubility in aqueous solution;
will have better physicochemical properties;
may have improved anti-cancer activity; and
may have an improved therapeutic index.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method for inhibiting tumor cells, inhibiting tumor growth or treating a cancer in a mammal, which method comprises administering to the mammal a salt of 4-(2,6-dichloro-benzoylamino)-1H-pyrazole-3-carboxylic acid piperidin-4-ylamide, said salt chosen from a methanesulphonate salt, an acetate salt and mixtures thereof, in an amount effective in inhibiting tumor cells, inhibiting tumor growth or treating a cancer.

2. A method according to claim 1, which method comprises administering to the mammal an acid addition salt of 4-(2,6-dichloro-benzoylamino)-1H-pyrazole-3-carboxylic acid piperidin-4-ylamide which is a methanesulphonate salt.

3. A method according to claim 1, for inhibiting tumor cells or tumor growth.

4. A method according to claim 1, for treating a cancer.

5. A method according to claim 1, wherein the tumor or cancer is selected from a carcinoma of the bladder, breast, colon, kidney, epidermis, liver, lung, oesophagus, gall bladder, ovary, pancreas, stomach, cervix, thyroid, prostate, or skin; a hematopoietic tumour of lymphoid lineage; a hematopoietic tumour of myeloid lineage; thyroid follicular cancer; a tumour of mesenchymal origin; a tumour of the central or peripheral nervous system; melanoma; seminoma; teratocarcinoma; osteosarcoma; xeroderma pigmentosum; keratoctanthoma; thyroid follicular cancer; and Kaposi's sarcoma.

6. A method as defined in claim 1, wherein the cancer is a leukaemia.

7. A method as defined in claim 1, wherein the tumor or cancer is selected from acute lymphocytic leukaemia, B-cell lymphoma, T-cell lymphoma, Hodgkin's lymphoma, non-Hodgkin's lymphoma, hairy cell lymphoma, and Burkett's lymphoma.

8. A pharmaceutical composition comprising an acid addition salt according to claim 1, together with one or more pharmaceutically acceptable carriers, adjuvants, excipients, diluents, fillers, buffers, stabilisers, preservatives, lubricants, and other therapeutic or prophylactic agents.

9. A combination comprising an acid addition salt of 4-(2,6-dichloro-benzoylamino)-1H-pyrazole-3-carboxylic acid piperidin-4-ylamide, said salt chosen from a methanesulphonate salt, an acetate salt and mixtures thereof, and one or more other therapeutic agents.

10. A combination according to claim 9, wherein said acid addition salt of 4-(2,6-dichloro-benzoylamino)-1H-pyrazole-3-carboxylic acid piperidin-4-ylamide is the methanesulphonate salt.

11. A combination according to claim 9 wherein the one or more other therapeutic agents are anticancer agents selected from:
   topoisomerase inhibitors
   alkylating agents
   antimetabolites
   DNA binders
   microtubule inhibitors (tubulin targeting agents)
   monoclonal antibodies and
   signal transduction inhibitors.

12. A combination according to claim 9 wherein the one or more other therapeutic agents are selected from cisplatin, cyclophosphamide, doxorubicin, irinotecan, fludarabine, 5FU, taxanes, and mitomycin C.

13. A method according to claim 1, comprising administering an acid addition salt of 4-(2,6-dichloro-benzoylamino)-1H-pyrazole-3-carboxylic acid piperidin-4-ylamide and one or more other therapeutic agents, wherein the one or more other therapeutic agents are administered either simultaneously or sequentially.

14. A combination according to claim 9 wherein the acid addition salt of 4-(2,6-dichloro-benzoylamino)-1H-pyrazole-3-carboxylic acid piperidin-4-ylamide, and one, two, three, four or more other therapeutic agents are formulated together in a dosage form containing two, three, four or more therapeutic agents.

15. A method according to claim 1 additionally comprising radiotherapy.

16. A method according to claim 13 wherein the one or more other therapeutic agents are anticancer agents selected from:
   topoisomerase inhibitors
   alkylating agents
   antimetabolites
   DNA binders
   microtubule inhibitors (tubulin targeting agents)
   monoclonal antibodies and
   signal transduction inhibitors.

* * * * *